(12) United States Patent
Avisar

(10) Patent No.: US 9,788,905 B2
(45) Date of Patent: Oct. 17, 2017

(54) METHOD AND SYSTEM FOR SIMULATING SURGICAL PROCEDURES

(75) Inventor: Mordechai Avisar, Highland Heights, OH (US)

(73) Assignee: Surgical Theater LLC, Elyria, OH (US)

( * ) Notice: Subject to any disclaimer, the term of this patent is extended or adjusted under 35 U.S.C. 154(b) by 817 days.

(21) Appl. No.: 14/008,917

(22) PCT Filed: Mar. 30, 2012

(86) PCT No.: PCT/US2012/031514
§ 371 (c)(1),
(2), (4) Date: Dec. 10, 2014

(87) PCT Pub. No.: WO2012/135653
PCT Pub. Date: Oct. 4, 2012

(65) Prior Publication Data
US 2015/0127316 A1 May 7, 2015

Related U.S. Application Data

(60) Provisional application No. 61/469,152, filed on Mar. 30, 2011.

(51) Int. Cl.
*G06F 19/00* (2011.01)
*A61B 19/00* (2006.01)
(Continued)

(52) U.S. Cl.
CPC .............. *A61B 19/50* (2013.01); *A61B 34/10* (2016.02); *G06F 3/04815* (2013.01); *G06F 17/5009* (2013.01); *G06F 19/321* (2013.01); *G06F 19/324* (2013.01); *G06F 19/3437* (2013.01); *G06T 13/20* (2013.01); *G06T 19/20* (2013.01);
(Continued)

(58) Field of Classification Search
None
See application file for complete search history.

(56) References Cited

U.S. PATENT DOCUMENTS 5,595,703 A   1/1997   Swaelens et al.
5,768,134 A   6/1998   Swaelens et al.
(Continued)

FOREIGN PATENT DOCUMENTS

CN   1720561 A   1/2006
CN   1973780 A   6/2007
(Continued)

OTHER PUBLICATIONS

Extended European Search Report; Applicant: Avisar, Mordechai; Application No. ep 12 76 2939; Place of Search: Munich; Date of Completion of Search: Aug. 11, 2015.
(Continued)

*Primary Examiner* — Mary Zeman
(74) *Attorney, Agent, or Firm* — Bodi Law LLC

(57) ABSTRACT

A system and method for converting static/still medical images of a particular patient into dynamic and interactive images interacting with medical tools including medical devices by coupling a model of tissue dynamics and tool characteristics to the patient specific imagery for simulating a medical procedure in an accurate and dynamic manner by coupling a model of tissue dynamics to patient specific imagery for simulating cerebral aneurysm clipping surgery.

21 Claims, 22 Drawing Sheets

(51) Int. Cl.
  *G06T 13/20* (2011.01)
  *G06T 19/20* (2011.01)
  *G09B 23/28* (2006.01)
  *G06F 3/0481* (2013.01)
  *G06F 17/50* (2006.01)
  *A61B 34/10* (2016.01)

(52) U.S. Cl.
  CPC ........ *G09B 23/28* (2013.01); *A61B 2034/102* (2016.02); *A61B 2034/104* (2016.02); *G06T 2210/41* (2013.01); *G06T 2219/2021* (2013.01)

(56) References Cited

U.S. PATENT DOCUMENTS

| | | |
|---|---|---|
| 5,826,206 A | 10/1998 | Nemeth |
| 6,037,927 A | 3/2000 | Rosenberg |
| 6,113,395 A | 9/2000 | Hon |
| 6,857,878 B1 | 2/2005 | Chosack et al. |
| 6,863,536 B1 | 3/2005 | Fisher et al. |
| 6,939,138 B2 | 9/2005 | Chosack et al. |
| 7,101,383 B1 | 9/2006 | Van Ess |
| 7,261,565 B2 | 8/2007 | Chosack et al. |
| 7,616,730 B2 | 11/2009 | Flohr |
| 8,311,791 B1 | 11/2012 | Avisar |
| 2001/0046935 A1 | 11/2001 | Okamura |
| 2002/0059284 A1 | 5/2002 | Bronstein et al. |
| 2004/0253572 A1 | 12/2004 | Chosack et al. |
| 2005/0032028 A1 | 2/2005 | Chosack et al. |
| 2006/0036167 A1 | 2/2006 | Shina |
| 2006/0085175 A1 | 4/2006 | Hartlep et al. |
| 2007/0129626 A1 | 6/2007 | Mahesh et al. |
| 2007/0134637 A1 | 6/2007 | Bronstein et al. |
| 2007/0141543 A1 | 6/2007 | Grund-Pedersen |
| 2009/0018808 A1 | 1/2009 | Bronstein et al. |
| 2009/0187393 A1 | 7/2009 | Van Lierde et al. |
| 2009/0311655 A1 | 12/2009 | Karkanias et al. |
| 2010/0009314 A1 | 1/2010 | Tardieu et al. |
| 2010/0092904 A1 | 4/2010 | Esposti et al. |
| 2010/0161076 A1 | 6/2010 | Pallari |
| 2010/0178644 A1 | 7/2010 | Meglan et al. |
| 2010/0191088 A1 | 7/2010 | Anderston et al. |
| 2010/0217336 A1 | 8/2010 | Crawford et al. |
| 2010/0305928 A1 | 12/2010 | Cohen et al. |
| 2011/0236868 A1 | 9/2011 | Bronstein et al. |
| 2012/0058457 A1 | 3/2012 | Savitsky |
| 2013/0047103 A1 | 2/2013 | Avisar |

FOREIGN PATENT DOCUMENTS

| | | |
|---|---|---|
| CN | 102354345 A | 2/2012 |
| JP | 2006509238 A | 3/2006 |
| WO | 9610949 | 4/1996 |
| WO | 2004029908 A1 | 4/2004 |
| WO | 2004051603 A1 | 6/2004 |
| WO | 2009059716 A1 | 5/2009 |
| WO | 2009094621 A2 | 7/2009 |
| WO | 2010030523 A1 | 3/2010 |
| WO | 2010132606 A1 | 11/2010 |
| WO | 2012135653 A1 | 10/2012 |
| WO | 2013177520 A1 | 11/2013 |
| WO | 2015154069 A1 | 10/2015 |

OTHER PUBLICATIONS

Toru Koyama M.D. et al.; Simulation of the surgical manipulation involved in clipping a basilar artery aneurysm; concepts of virtual clipping; J. Neurosurg.; vol. 93; Aug. 2000.

PCT International Search Report; International Application No. PCT/US2012/031514; International Filing Date: Mar. 30, 2012; Date of Actual Completion of International Search: Jun. 8, 2012; Date of Mailing of International Search Report: Jul. 12, 2012.

Toru Koyama M.D. et al.; Simulation of the surgical manipulation involved in clipping a basilar artery aneurysm; concept of virtual clipping; J. Neurosurg.; vol. 93; Aug. 2000; parts "Description of Model and Method", "Results".

Joanna Leng; Scientific Examples of Virtual Reality and Visualization Applications; Manchester Research Center for Computational Science; Mar. 2001; part "Surgical Simulation".

M.A. Padilla et al.; Computer Simulation of Prostate Surgery; Universidad Nacional Automoma de Mexico; Oct. 15, 2007.

Montgomery, K. et al; Studies in Health Technology and Informatics; "Spring: A General Framework for Collaborative, Real-time Surgical Simulation"; 2002, vol. 85, pp. 296-303.

Qin, J. et al; Studies in Health Technology and Informatics; "An Adaptive Framework Using Cluster-Based Hybrid Architecture for Enhancing Collaboration in Surgical Simulation"; 2007, vol. 125, pp. 367-372.

Architecture and workflow of SRP.

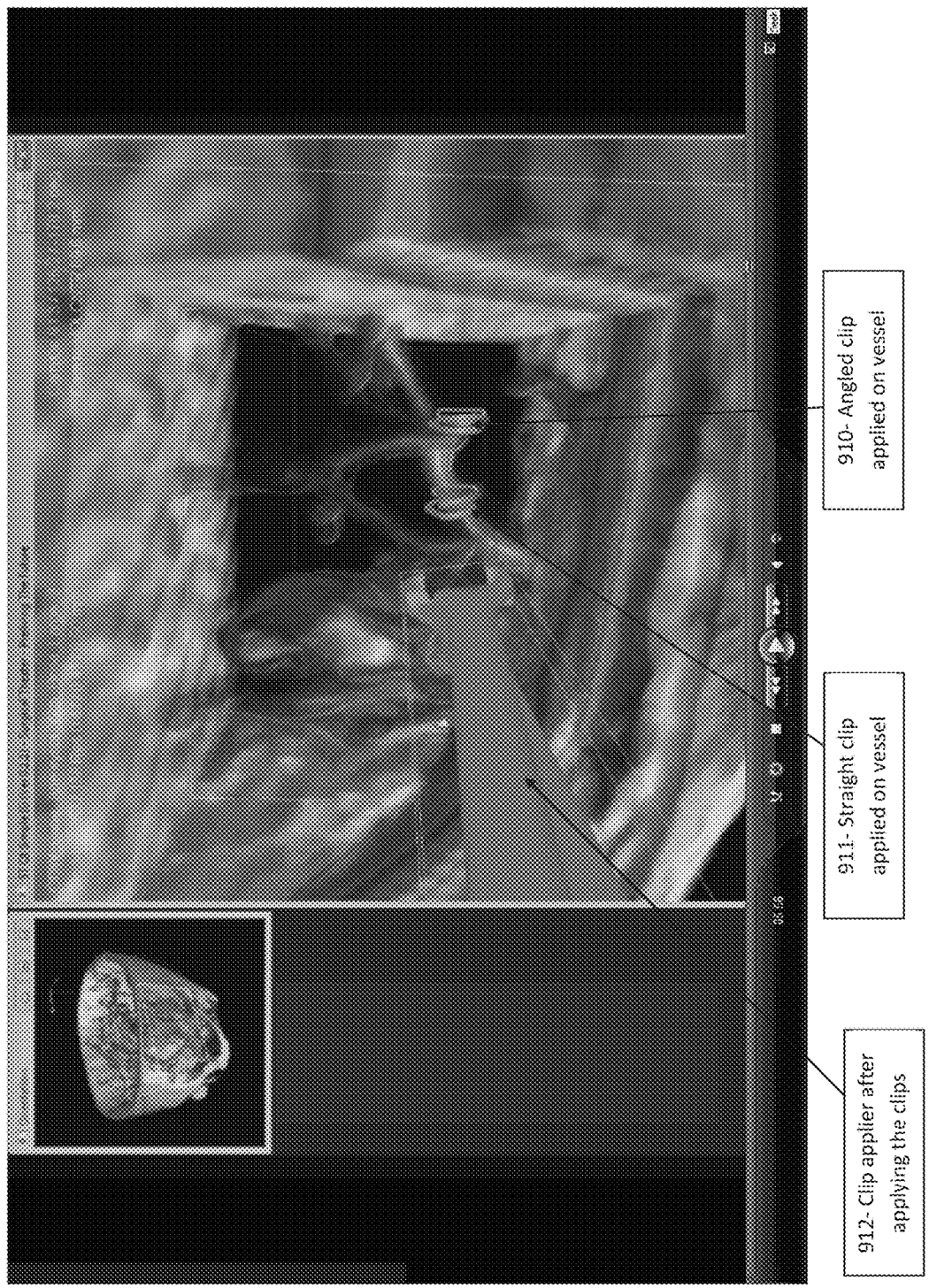

METHOD AND SYSTEM FOR SIMULATING SURGICAL PROCEDURES

CROSS-REFERENCES TO RELATED APPLICATIONS

This application is a national stage application of PCT international application PCT/US12/31514 filed on Mar. 30, 2012, which claims the benefit of U.S. Provisional Application Ser. No. 61/469,152 which was filed on Mar. 30, 2011 both of which are incorporated herein by reference.

BACKGROUND OF THE INVENTION

This application relates generally to a system and method for simulating surgical procedures. More specifically, this application relates to a system and method for converting static/still medical images into dynamic and interactive images interacting with medical tools (such as, e.g., surgical tools, probes, and/or implantable medical devices) by coupling a model of tissue dynamics to patient specific imagery for simulating cerebral aneurysm clipping surgery.

"Medical errors kill as many as 98,000 people annually at a total national cost of between $37 to $50 billion for adverse events and between $17 to $29 billion for preventable adverse events." "Surgical errors are the leading medical error" Source: *To Err Is Human: Building a Safer Health System*, Institute of Medicine. National Academy of Sciences. (1999).

Furthermore, out of 19,034 treated cerebral aneurysm cases in U.S. non-government hospitals between 2002-2006, 10,719 (56%) were treated by cerebral aneurysm clipping surgery. Even with the advent of endovascular techniques, the more complicated aneurysms still require microsurgical clipping.

During the course of high risk surgeries, such as, cerebral aneurysm repair surgeries, for example, the absolute orientation of the brain tissues is significantly altered as a surgeon pushes and cuts tissues to approach the aneurysm area. Therefore, the current utilization of the advanced surgery preparation and aiding systems such as Image Guided and Navigation Systems which are based on pre-registered 3D imageries, are limited in assisting the surgeons. Also, surgeries, such as aneurysm repair, are extremely time-sensitive, for example, due to various procedures including temporary vessel clamping to the aneurysm area. Therefore, the efficiency of the procedure is highly critical and detailed planning based on the patient specific local geometry and physical properties of the aneurysm are fundamental. To achieve a new level of pre-surgery preparation, 3D CT and MRI images are being increasingly utilized. However, those images offer only minor benefits, standing alone, for surgery rehearsal.

Surgeons lack a rehearsal and preparation tool that would provide them with a realistic visual model with physical tissue properties. Currently, there is no capability for pre-surgery preparation that allows a neurosurgeon to plan and physically rehearse the microsurgical strategy based on the patient-specific anatomy of the aneurysm. Hence, it is desired to have a "full immersion" surgical tool that encompasses: (i) realistic "life-like" 3D display of the patient-specific area of surgery (such as supporting cerebral aneurysm clipping surgery); (ii) modeling of the local patient-specific area of surgery geometry and physical properties; (iii) interface enabling manipulation of the patient-specific area of surgery model and virtually perform surgical actions such as cutting, shifting and clamping; and (iv) interface to provide feedback cues to the surgeon.

SUMMARY OF THE INVENTION

The disclosed system and method, called the "Cerebral Aneurysm Surgery Rehearsal Platform" (CA-SRP), provides a platform that allows a neurosurgeon to plan and physically rehearse the microsurgical strategy based on the patient-specific anatomy of the aneurysm. As a unique surgery preparation system, the CA-SRP provides patient-specific: (i) accurate modeling of the tissue mechanical properties; (ii) realistic 3D imagery of the tissues (as seen in open/classic surgery); and, (iii) real-time, surgery-like manipulation of the dynamic and interactive 3D tissue models (v) dynamic and interactive modeling of surgery tools including aneurysm clips, implants, and other devices, integrated into the 3 dimensional dynamic and interactive patient specific case. Accordingly, the CA-SRP provides the following clinical benefits for the patient, the surgeon, and the hospital: (i) reduced potential for objectively assessed intra-operative errors during microsurgical clipping; (ii) improved potential for neurosurgeon's insightful and successful response to adverse events; and, (iii) decreased operative time.

Provided is a modeling system for performing a surgical simulation, comprising: a database for storing patient tissue image information that are taken from, or derived from, medical images of a particular patient; the database also for storing standard characteristics of the tissue; a display; an image generator for generating a dynamic 3D image of tissues of the particular patient for display on the display, the generating utilizing the patient image information such that the dynamic 3D image of tissues realistically represents corresponding actual tissues of the particular patient; a tool interface for connecting to a real surgical tool adapted for use with the modeling system; a user tool generator for generating a tool model of a user tool for dynamically interacting with the 3D image of tissues via manipulations provided by a user; and a user interface for the user to adjust parameters of the modeled tool, wherein the tool model is displayed on the display dynamically interacting with the 3D image of tissues according to the adjusted modeling parameters for realistically simulating the medical procedure.

Also provided is a modeling system for performing a simulation of an aneurysm clipping surgery, comprising: a database for storing patient tissue image information that are taken from, or derived from, medical images of a particular patient, the image information including an aneurysm; the database also for storing standard characteristics of the tissue; a display; an image generator for generating a dynamic 3D image of tissues of the particular patient for display on the display, the generating utilizing the patient image information such that the dynamic 3D image of tissues realistically represents corresponding actual tissues of the particular patient and includes at least one blood vessel showing an image of the aneurysm in 3D; a memory for storing a library of a plurality of models of different aneurysm clips to the user; a user interface for selecting one aneurysm clip model from the plurality of models for use as the aneurysm clip model for dynamically interacting with the image of the aneurysm; a tool interface for connecting to a real aneurysm clip applier adapted for use with the modeling system; an interface for the user to adjust the mechanical properties of the image of the aneurysm; and a user tool generator for generating the selected aneurysm clip for dynamically interacting with the image of the aneurysm via manipulations of the real aneurysm clip applier by a user, wherein the aneurysm clip is displayed on the display dynamically interacting with the image of the aneurysm based on the mechanical properties of the image as adjusted by the user for realistically simulating the aneurysm clipping surgery.

Also provided are additional embodiments of the invention, some, but not all of which, are described hereinbelow in more detail as example embodiments.

BRIEF DESCRIPTION OF THE DRAWINGS

The features and advantages of the examples of the present invention described herein will become apparent to those skilled in the art to which the present invention relates upon reading the following description, with reference to the accompanying drawings, in which:

FIGS. 10A-10C are example screen-shots of an example rendered 3D tissue model of the CA-SRP interface.

DETAILED DESCRIPTION OF THE EXAMPLE EMBODIMENTS

Figure 1:
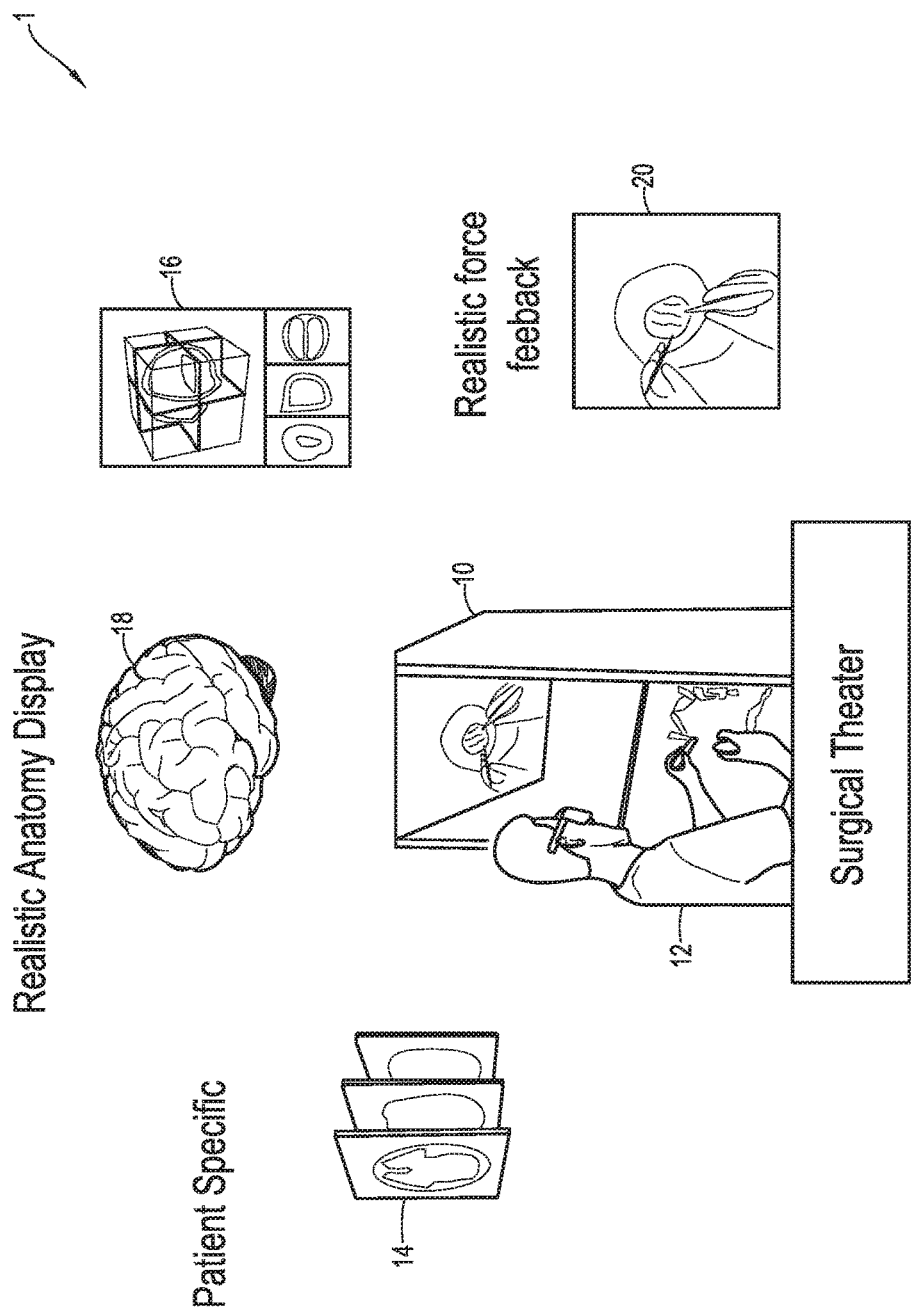
FIG. 1 provides a high-level schematic of an example Surgical Theater.

As a Commanding General of the US Army Medical Research and Command, General Lester Martinez-Lopez declared, "I look forward to the day when simulation can be leveraged to its fullest extent to reduce medical errors, improve medical skills, and, above all, improve medical care for patients". The importance of the General's vision is emphasized in the sobering medical statistics: "Medical errors kill as many as 98,000 people annually at a total National cost of ~$37 to $50 billion for adverse events and ~$17 to $29 billion for preventable adverse events". From the perspective of a neurosurgeon Dr. El-Kadi M.D., Ph.D. explains, "Even the most routine surgical procedure has the potential for complications". He further reflects: "the most difficult part for me is how I prepare the case in my mind. For me, going to surgery is like going to war. You must identify your mission, be very well prepared, flawlessly execute your plan, and then return home safe. If you're not prepared, then you should not go". Indeed, the highest level of surgeon's preparedness is required for performing high-risk surgeries, (e.g. cerebral aneurysm repair) where crucial decisions are made under severe time constraints, which are dictated by the biological importance and fragility of the brain and surrounding structures. In other words, the surgeon's preparedness is essential to avoid potentially devastating consequences and maximize the success of the clinical outcome. This creates a critical need to increase the potential for a successful surgical outcome through avoidance of objectively assessed intra-operative errors and tactical refinement of patient-specific surgical procedures, particularly in the field of neurosurgery. Thus, providing the neurosurgeon with the ability to iteratively plan and physically rehearse the course of a particular neurosurgery without risk to the patient will substantially reduce surgical errors thereby increasing the likelihood of a successful surgical outcome.

Currently, 3D CT/MRI scans are increasingly utilized in an effort to achieve a better level of surgical preparation, (6-11). However, during the course of a brain surgery, the absolute orientation of brain tissues is significantly altered as the surgeons cut, retract, and dissect tissues. Present utilization of "advanced" surgery aiding systems, which are based on pre-registered static 3D images, provide limited pre-surgery assistance to surgeons since these systems are not capable of projecting the changes in tissue orientation and do not provide any tactical rehearsal capabilities. Previous research in commercial and military aviation has clearly demonstrated that rehearsal prior to task performance can result in significant improved outcomes (12; 13). Unfortunately, as stated above, these pre-mission (or pre-surgery) simulation and training tools have been noticeably absent in healthcare. The CA-SRP allows neurosurgeons to develop, rehearse and refine the tactical strategies for patient-specific cerebral aneurysm clipping surgery. Major complications that can result from this procedure include, among others, premature aneurysm rupture, postsurgical stroke or "rebleeding" from improper clip placement. Furthermore, as certain phases of the aneurysm repair are extremely time-sensitive (e.g. temporary vessel occlusion of afferent vessels), the efficiency of the procedure is highly critical. This emphasizes the importance for detailed planning and the need for tactical rehearsal capabilities based on the local geometry and physical properties of the patient-specific aneurysm.

The disclosed system and method (hereinafter the "Cerebral Aneurysm Surgery Rehearsal Platform" (CA-SRP)) utilizes an improvement of the Surgical Theater system disclosed in U.S. patent application Ser. No. 12/907,285 that was filed on Oct. 19, 2010, and is hereby incorporated herein by reference. The Surgical Theater is a computerized system that convents medical images into dynamic and interactive images by coupling a model of a specific tissue's dynamic attributes to patient specific imagery. This dynamic and interactive image/model creates a new, novel, and original standard for medical imagery and has many applications. Among others, the system/method can be utilized by medical imagery navigation systems and image guided and robotic surgery systems that can enhance their planning performances by utilization of Surgical Theater dynamic and interactive tissue models coupled with the patient specific imagery.

The Surgical Theater address challenges in surgeries that involve high-risk activities, such as heart and brain surgeries including valve repair and replacement, bypass surgeries, brain tumor removal, Aneurysm clipping, and others.

For example, in the case of open/classic brain surgeries, such as brain tumor and brain aneurysm, for example, the Surgical Theater converts CT and MRI images and creates a realistic three dimensional (3-D) model of the brain tumor or aneurysm area with a dynamic modeling of the organisms, including the tumor, along with the surrounding tissue and blood vessels. The system is connected to life-like surgery tools, responding to actions taken by the surgeon, helping him/her to better prepare for the surgery. The Surgical Theater system simulates realistic events such as brain swelling, damage to blood vessels, brain tissue shifting during an operation blocking access to the remaining parts of the tumor, among others. The system can be used as a planning and preparation tool, allowing surgeons to tailor a specific surgical strategy for a given case, maximizing the surgery efficiency while minimizing the risk.

Surgical Theater System Overview

FIG. 1 provides an example embodiment for one application of the system 1 where a patient specific scan image (CT, MRI or similar) (14) is fed to the system's console (10), an algorithm that creates a 3 dimensional realistic anatomy display (18) adds texture, shadow, shadowing and other cues to the image, a mechanical properties algorithm (16) assigns mechanical behavior characteristics to the image and transfer the image from static/still image to a dynamic and interactive image/model. Interfaces with or without force feedback (20) are connected to the system allowing the surgeon/operator (12) to manipulate the image/model that the system creates; the surgeon can select tools and implants from libraries of tools and implants including characteristics of those tools and implants. The surgeon then performs a virtual surgery on a manipulateable, dynamic and interactive 3 dimensional image/model of his patient organism in a realistic and dynamic manner.

The system includes an executive program that runs and manages all the system components and updates the status of the sub components according to the surgeon/operator (12) actions. For example, when the surgeon uses the interface (20) to push a tissue (such as by using a chose tool) that he sees in the display (18), the mechanical properties model (16) receives the information regarding the force that was applied, e.g., the direction of force; the tool that is being used including its material and shape and other mechanical characteristics of the tool, then the mechanical properties are used to calculate a new state of the 3 dimensional orientation an ad setup of the image according the force that was applied, the executive program send the calculated 3 dimensional matrix to the realistic anatomy display (18) that was created by the mechanical properties algorithm (16), the realistic anatomy display calculates the new image and its cues due to the change of image e.g., a new set of shadows and shadowing due to the new orientation of the image components are determined. Simultaneously, the mechanical properties model (16) send a set of parameters to the force feedback interface (20), these parameters include information of the force that the surgeon/operator (12) needs to sense due to the interaction with the organs (the force that the organ returns after the surgeon pushes or otherwise interacts with the tissues). This process of calculation of new stage at each one of the system's components (14, 16, 18, 20) is executed rapidly and continuously in cyclic manner, and each cycle is completed within a frame time of milliseconds, allowing the surgeon/operator to receive real-time and realistic cues and real-time reactions to his actions.

Figure 1A:
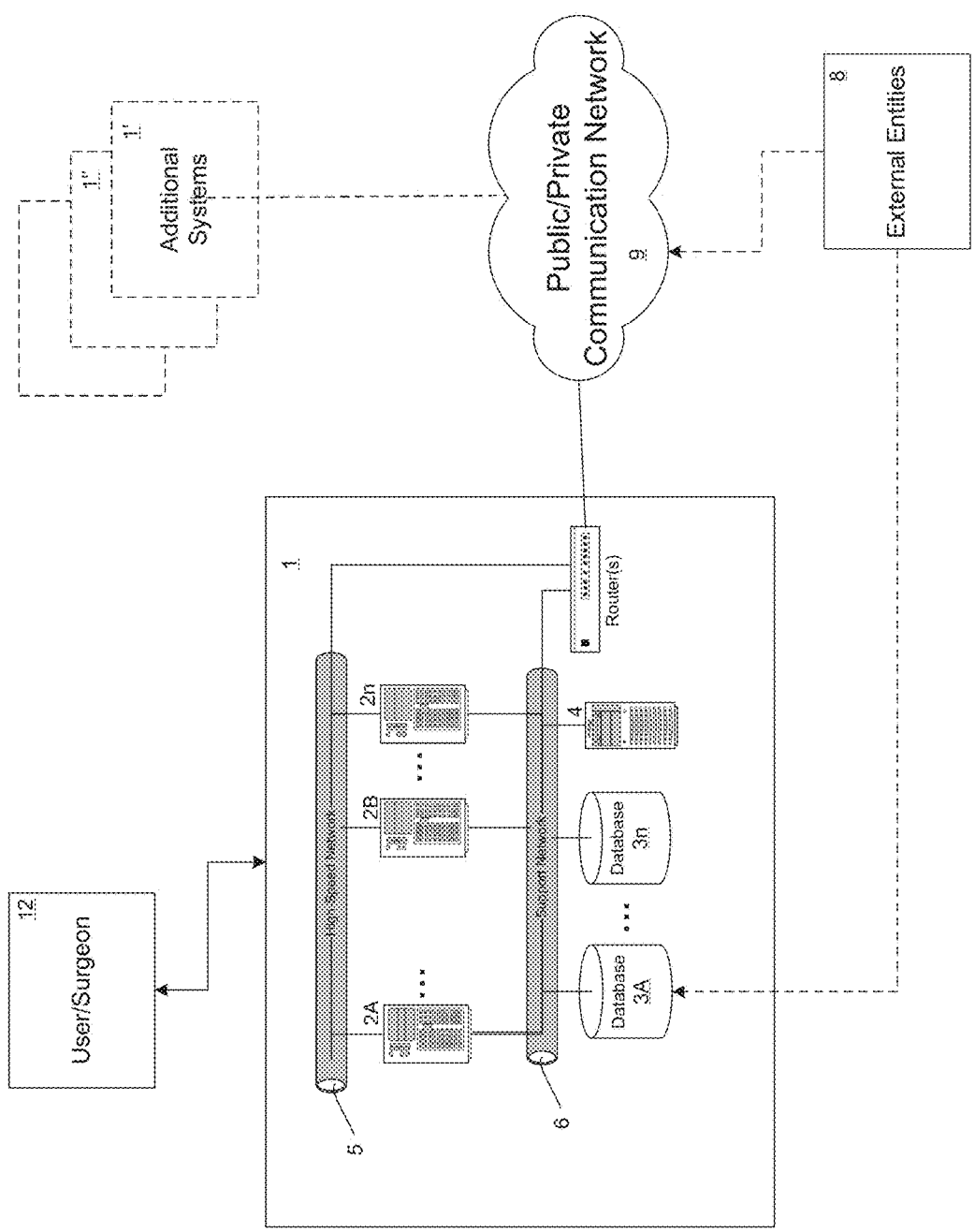
FIG. 1A provides another high-level schematic of a hardware implementation of the example Surgical Theater.

The Surgical Theater is a system, as shown in FIG. 1A, that integrates several computers (PCs) 2A-2n, one or more databases 3A-3n and other hardware components (e.g., networks 5, 6) and proprietary software into one complete system 1 (see both FIGS. 1 and 1A) that is structured into an immersive chamber/console sized about as big as a small walk in closet (see console 10 in FIG. 1). Once the surgeon 12 starts the system, the surgeon loads the set-up parameters of his patients which include details of the patient to allow the system to up-load the relevant data, the Surgical Theater than loads all the patient's available CT and MRI images from a patient images 14 into the database(s) 3 and other information that concern the simulated models such as patient age, gender and so on (some or all of which may be obtained from external entities 8, such as medical databases, for example). The system utilizes tissue information parameters 16 from a system database. The system 1 performs a segmentation process and identified the Entities of the organ, Entities are vessels, tissue, tumor, and so on to create the simulated image model 18 shown to the surgeon on the display of the device. The system provides realistic tactical feedback 20 via feedback mechanisms to add further realism to the simulation.

The system applies the layers of the realistic visual, the mechanical properties and other relevant parameters 16 from the system database(s) and characteristics relevant to the case, all applied on the top of the CT and MRI images 14 from the patient images database(s) 3 and synchronized with those images. The synchronization creates, for example, vessel mechanical properties that are 'clamped' or 'attached' to the vessel images and so on to provide realistic simulation capability. The surgeon can be provided the ability to "fine tune" the models and adjust the mechanical properties of a certain area of the organ. For example, the surgeon may adjust the elasticity and other mechanical characteristics of the Entities behavior.

Subsequently, after such a set-up, the Surgical Theater projects the 3 dimensional organ model 18 presented in a realistic visual fidelity with realistic features such as; texture, shadowing and other features that adds realism to the simulated image. Each segment of the visual model 18 is coordinated and corresponds with an appropriate mechanical properties model from the system database 16 and other relevant properties of the specific case.

At this stage, the system allows the surgeon to browse and chooses from the system's virtual libraries 16 in the system database the relevant surgery tools and other elements (in the system software terms those tools and elements are "Entities" as well) that he may need to perform the surgery (or other procedure). Such elements may include; seizers and clamps, clips for aneurysm, artificial heart valves, and other elements appropriate for the specific case. (Adding additional systems 1', 1" . . . connected to the system 1 via a network 9—such as over the Internet or a private network— can result in a collaborative theater platform, described in more detail later in this disclosure.)

All of the various Entities are represented by the system in high-fidelity distributed models and functioning in a distributed architecture, e.g., each Entity typically has a separate subEntity, where the subEntity is, for example, a "visual entity" or "mechanical entity" and so on. Each subEntity exists in one of the different environments (e.g., the visual system environment, the mechanical modeling environment and so on, described in more detail below) distributed among a plurality of computers. Each such subEntity is responsible for its own performance (i.e. presenting the realistic visual of the Entity, or performing the Entity's mechanical operation, for example).

The subEntities communicate via a distributed network (described in more detail below) to synchronize and coordinate the subEntities into a one integrated Entity compound model. For example, when a tissue is being pressed by a surgery tool, the surgery tool pressure characteristics (e.g., the location, orientation and amount of pressure and so on) is distributed via the network, each one of the subEntities is responsible for 'listening' and concluding if it is being affected by this surgery toll pressure; once a subEntity determines that it is being affected, each such subEntity (for example, tissue Entity) models the affect on their subEntity model, e.g., the visual subEntity, presents the visual effects (such as bloodiness of the tissue), and the mechanical properties models the shift of the tissue. Each subEntity distributes the change—for example, the tissue location and dimension changes—over the network so the other subEntities will be able to determine if they are being affected by this change. At the end of such action, all the subEntities of the tissue for the above example, (and the other Entities), become accustomed to, and, if needed, adapt their states and the models to, the new action that was sourced and initiated, in the above example, by the surgery tool.

Thus, the various functions (subEntities) can be distributed among various computers connected in a peer-to-peer network utilizing distributed data and state duplication (for keeping local copies of the state of the simulation), all listening on the network for any action that impacts their portion of the simulation, in which case they update their parameters via the network to keep the system accurate, which may, of course, impact other functions in other subEntities, which will therefore catch that fact by their monitoring of the network, leading to further updates, and so on. In this way, the system distributes the functionality among many computers in a parallel fashion so that updating can occur much quicker than it could if only a single computer were used. Only those subEntities impacted by a change need respond, and thus network traffic can be reduced to essentials.

The Surgical Theater allows the surgeon to record his actions and save them for later playback, to demonstrate his surgery plan to the chief surgeon or resident, or, to share information with other surgeons, demonstrate new techniques he is working on, practice the surgery, and so on. The system's interfaces to the surgeon includes surgery interfaces (e.g., seizers handles) that include force feedback that is delivered to those tools to allow the surgeon to sense the force feedback cue of his actions, realistically simulating an actual procedure.

Once the surgery tools and the other Entities are selected by the surgeon, they are integrated into the virtual surgery scene and turn into an integrated element of the simulated scenario including realistic visuals features and mechanical properties and operation properties features that are applied to each one of those selected items. For example, the simulated scissors reflect mechanical characteristics of real scissors and will cut in the simulation as the real scissors do, and, aneurysm clips, when placed at the simulated vessel, simulates blocking the blood flow.

Next, the surgeon performs the surgery actions at any stage of the virtual surgery; the surgeon can "freeze" the simulation and rotate the organ to observe the area of his interest from different orientations and perspectives. The surgeon can "mark point of time" of the virtual surgery and can command a "return to the mark point". For example, the surgeon can mark the time before clamping an aneurysm and return to this point of time while "un-doing" all the actions that took place after this point of time. In this fashion, the surgeon can evaluate different surgery approaches of a selected phase of the surgery without restarting the entire surgery from the original starting point. Several such 'mark points' are available allowing the surgeon to return and "re-do" actions and exams/rehearse on several selected phases of the surgery. Surgical Theater use may include surgeon rehearsals toward a surgery; surgeon demonstration to the chief surgeon or resident; surgical practice and development, testing, and validation of tools and methods, and knowledge sharing.

Collaborative Theater

Figure 2:
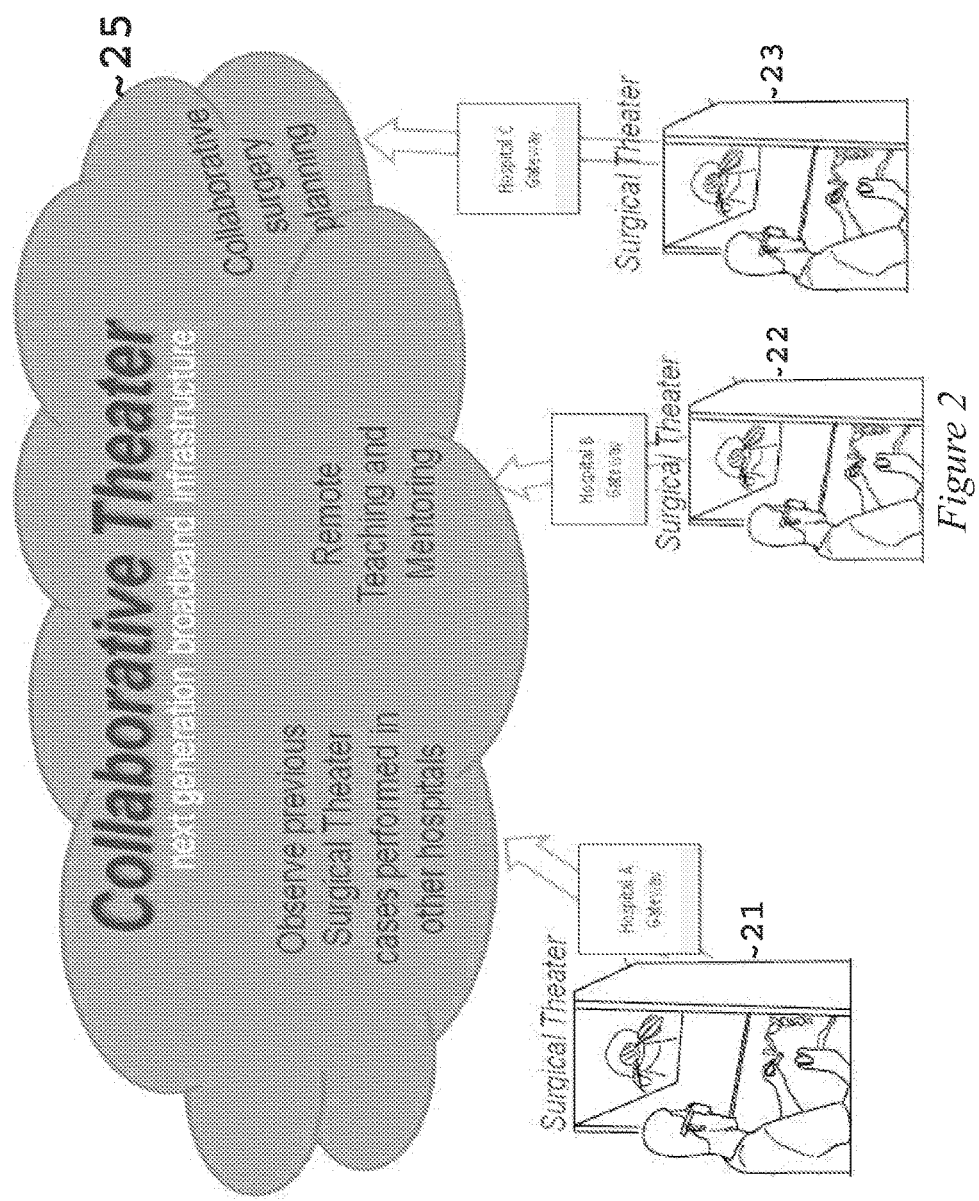
FIG. 2 a high-level diagram of an example of the Collaborative Theater concept.

FIG. 2 shows a high-level example implementation of the Collaborative Theater concept that was introduced with the Surgical Theater. By leveraging next generation broadband infrastructure 25, individuals using SRPs 21, 22, 23 . . . from different hospitals will be connected allowing surgeons across the nation and across the globe to collaboratively plan a surgery case, e.g., surgeons from two or more distributed sites step into their SRP and rehearse, together, on a patient case toward a surgery. This Collaborative Theater allows surgeons to study the best practice methods by observing previous Surgical Theater cases as well as providing remote teaching and mentoring. The Collaborative Theater allows all the hospitals that are connected and using the SRP to gain access to the up to date accrued knowledge and most recent "best practices".

System Level Design

The system level design description is outlined in the preceding sections. The visual rendering engines analyze 3D MRI and CT patient-specific images and create computerized segmented modules that represents the anatomical structures and features of the particular image. The medical market has a vast number of advanced Digital Imaging and Communication in Medicine—DICOM (1) viewers. Their feature sets range from layered black and white slices in 3 different panels that could be cross-referenced to a complete ability to fly through static subsets of 3D images of patient's organs. In addition, there are 4D and 5D features that record various functional and dynamic changes of organs in a form of a movie clip. As magnificent as those captured images or moving sequences might be, they are a fixed set of snapshots images in time.

The Surgical Theater takes existing 3D conversion processes and adds the features specific to the human tissues and structures based on physical and mechanical properties that are then stored in the system database. Once this patient-based model is set in motion in the virtual world, the Surgical Theater introduces a set of virtual surgical tools that allow the surgeon to manipulate (push, cut, clamp, etc.) those models similar to real surgery tissue manipulation, providing an intuitive experience for the surgeon.

Figure 3:
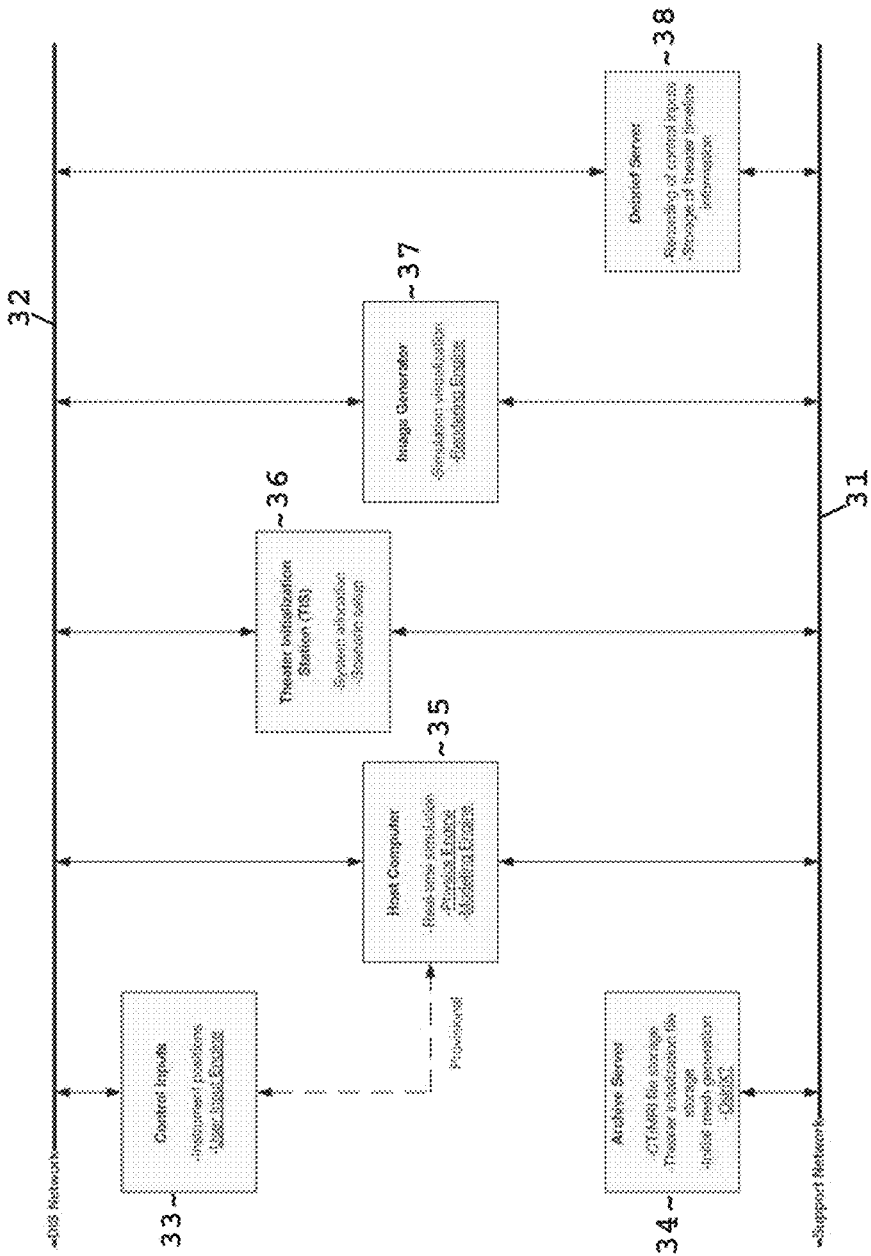
FIG. 3 shows an example breakdown of a distributed simulation network concept for the example Surgical Theater embodiments.

FIG. 3 provides a breakdown of an example Surgical Theater distributed simulation network (Surgical Theater DIS (ST-DIS) is presented). Each of the components (i.e., blocks) in the figure is an isolated computation station (that can be executed on a stand-alone computer or collection of computers) with a designated set of functions. The stations are appropriately connected with a regular support network 31 (such as an Ethernet network, for example) that handles slow irregular traffic, like transferring of vast amounts of DICOM data. Upon more intense data processing demand, the stations are supported by a specialized Distributed Interactive Simulation (ST-DIS) Network 32 that is a hardware isolated network used only for high priority simulation data (which can be implemented in high-bandwidth Ethernet, for example). The ST-DIS Network 32 carries volatile simulation information and allows for such an exquisite simulation load distribution.

The Surgical Theater's ST-DIS is a network architecture for building large-scale virtual worlds from a set of independent simulator nodes. The simulator nodes 33-38 are linked by the networks and communicate via a common network protocol (such as TCP/IP, for example). The ST-DIS infrastructure enables various simulators to interoperate in a time and space coherent environment. In the Surgical Theater's ST-DIS ST-DIS system, the virtual world is modeled as a set of "Entities" that interact with each other by means of events that they cause. The simulator nodes 33-38 each independently simulate the activities of one or more of the Entities in the virtual world of the simulation and report their attributes and actions of interest to other simulator nodes via messages on the network. The other simulator nodes on the network are responsible for "listening" to the network messages, determining which ones are of interest to them (based on the Entities they are simulating) and responding appropriately.

One of the features of the ST-DIS network and simulation architecture concerning distributed interactive simulation is that there need be no central server or processor. Each simulation application maintains its own copy of a common virtual environment in its own memory or database. Representations of this environment are distributed by various means to all simulation applications prior to any real time operation. ST-DIS is basically a peer-to-peer architecture, in which data is transmitted available to all simulators where it can be rejected or accepted depending on the receivers' needs. By eliminating a central server through which all messages pass, ST-DIS reduces the time lag for a simulator to send important information to another simulator. This time lag, known as latency, can seriously reduce the realism, and therefore the effectiveness, of a networked simulator. Effective distributed simulation depends on very low latency between the time that a new state/event occurs for a simulated entity to the time that the state/event is perceived by another entity that must react to it. Any delay introduced by the training device could result in negative reinforcement to the trainee.

Referring again to FIG. 3, the Archive Server 34 is generally used to perform the tasks of downloading and retaining in a database large amounts of data necessary for simulation. In addition, the Archive Server 34 can be used to prepare obtained data for further use in the simulation. Note that because its duties are typically global in nature, and not critical to the simulation activity, the Archive Server 34 is typically only connected to the support network 31.

FIG. 3 shows a network architecture that includes an off line "support" network (31) that "Archive Server" (34) that loads the medical images (CT/MRI) and additional initialization data stored in a database (for example, the patient name, age and so on and files to be included in the scenarios such as surgery tools libraries) "Debrief Server" (38) that records control inputs and store the scenarios and all the actions in a timeline information and allows playback of scenarios and actions. The real time network (32) is the network that transfers messages between the systems node during the simulation in a real time fusion—one way for implementing this network can be a Distributed Interactive Simulation (DIS) network (32), the components that connected to this network are; Control Input (33) that connected to the surgeon/operator systems interfaces, this node has an optional direct physical connection to the Host Computer (35) that may be implemented in a case that the real time requirements of the system cannot be satisfied by the DSI network and a direct physical connection between those nodes is needed. The Host Computer (35) includes the executive manger program and other models and simulation components and it is responsible for the real time synchronization and timing of the entire systems.

The Theaters Initialization Systems (TIS) (36) performs that system allocation and setup for each one of the nodes, for example, when the surgeon select a specific tool to use, the TIS allocates/activates the appropriate models of this tool for generating an accurate tool simulation (with tool characteristics stored in a database) for all the nodes assuring that all the nodes are set up with the same initialization. The Image Generator (36) performs the rendering and visualization tasks of the scenarios. The Host Computer (35), the TIS (36), the Image Generator (36) and the Debrief Server receive and exchange information with off line for initialization from the Support network (31) and receive and exchange information with the real time network (32) for "on line" and real time simulation.

Needed organ surface and volume data are extracted from an existing MRI/CT scan stored in the database. To obtain 3D organ surface data, the system can use a DICOM viewer and data management system such as the OsiriX (or comparable) that is open source software implemented for Apple Macintosh computers, for example. By "tapping into" OsiriX's ability to generate 3D surfaces of organs and organ groups based on the voxel density values with Objective C source code, the Surgical Theater adds an ability to store information about the 3D surfaces and organ types that describe into a flat file in a database. The entire set of parts of this study stored in this manner in the system database so that it is later transferred to the Image Generator Station 37 that recreates the patient-specific images based on standard characteristics of the organs. Once the necessary rendering data is obtained, the rendering platform for Image Generator Station 37 is applied to the image. For this, a proprietary Image Generator algorithm is integrated (such as a Flight IG; see the features in the separate headings for the Realistic Image Generator—RIG) with a Visualization Tool Kit.

The IG has unique features that deliver fine cues such as shadowing, texture, and material properties that are assigned to the visual models and as further detailed in the RIG sections. Not only does the IG create realistic and fully immersed environments by using those features, it can also process large volume of visual data base models under hard real time constraints. Enabled by the combination of the DIS architecture and the "Entity" design, the network traffic is minimized and the anatomy of the peer-to-peer nodes create a highly efficient real time system.

After the patient-specific images have been successfully rendered, various physics libraries are added in order to create proper simulation. Pushing and manipulation of the brain tissue is simulated using extensive research embodied in modeling platforms such as the OpenTissue (or comparable) collections of libraries that are available. The Open-Tissue, for example, is an open source collection of libraries that models volumetric shells and other complex behavior of 3-dimensional shapes. Customized libraries can also be developed for use. Specificity of the brain tissue physics and mechanics properties that derived from the research of mechanical properties of brain tissue in tension can be utilized, for example. Experimental papers are available that provide mathematical models of the mechanical manipulation of animal brain samples. Dynamic and realistic interaction of simulated surgical tools with the simulated tissues are implemented in the algorithms and approaches as described by Viet H Q H, Kamada T, and Tanaka H T, *An algorithm for cutting* 3*D surface meshes* and/or volumetric models, 18th International Conference on Pattern Recognition, 4, 762-765. 2006 (incorporated herein by reference). The work looks at various tools and tissue types to create a realistic simulation specifically for implementation of surgical simulations.

The software code of the example Surgical Theater is written in a commercial environment such as C++, with the code being designed to run in windows operating system, a Linux system, or compatible. In the coding development process, emphasis is given for the code real time execution and code efficiency all aimed to maintain a real time system performance while minimizing the latencies.

The visual system driver located in the Image Generator (37) is designed with an optimizers environment, such as OpenGL or similar, enables high-performance rendering and interaction with large models while maintaining the high model fidelity demanded, providing attention to detail while maintaining high performance in a cross-platform environment.

For computing efficiency purposes, each of the visual model's Entities have several Level of Details (LOD) representations; high LOD is presented in areas of the simulation scene in which the surgeon needs high resolution at, and, lower LOD is presented in areas of the simulation scene in which the surgeon has no immediate interest or interaction with. For example, tissue visual model is presented in high LOD in the area around the surgeon interaction and with lower LOD in areas that the surgeon doesn't have immediate interaction with. The LOD can be dynamically adapted: a surgeon's actions such as pointing the surgery instruments toward a specific area can be utilized by the LOD optimization algorithm for the dynamic allocation of the LOD for specific section of the visual models.

The typical system's computer is a PC with a multiple core (multiple processors) which provides flexibility and growth potential. The computer system includes random access memory, Ethernet ports, system disk, and data disk.

For the validation of the Surgical Theater (image quality, realism, image controller and manipulation), the skills and experience of senior surgeons are utilized. The surgeons are used to evaluate the system by performing specific surgical procedure while comparing it against their vast neurosurgical experience as well as against a specific case that they have already operated and is being simulated in the Surgical Theater.

Figure 4:
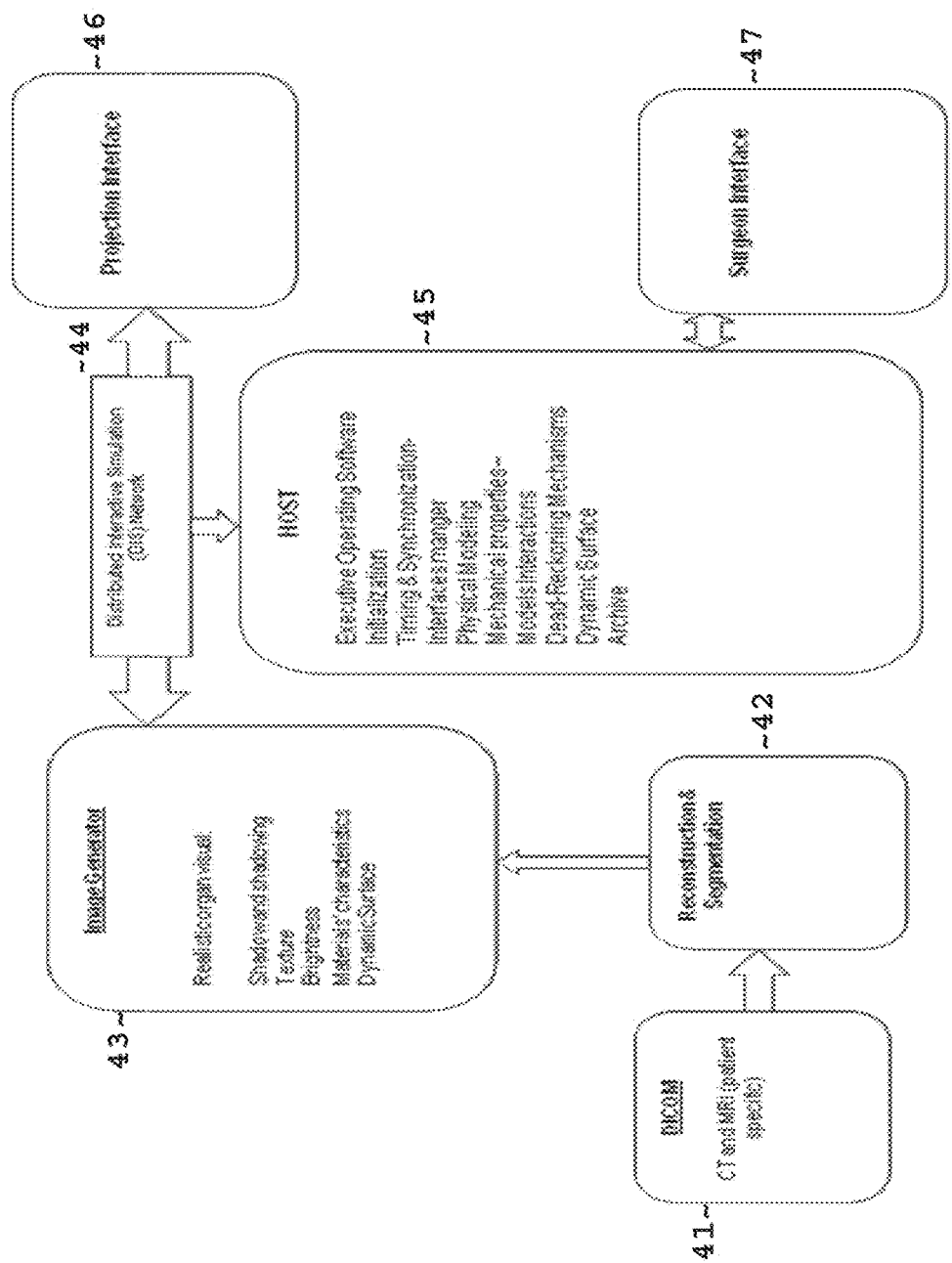
FIG. 4 is a block diagram block diagram showing design level and preliminary software design requirements for the Surgical Theater.

The Surgical Theater Block Diagram of FIG. 4 describes the functionality and the flow of the process (vs. the actual network connection of FIG. 3) from the row data of the scanted image DICOM 41 through the process of segmenting the row data (to identify soft tissue, vessels and so on). Then the Image Generator assign visual representation of each segment (shadow texture and so on), this image is connected via the DIA 44 network to a projection interface 46 and to the Host 45 that will update the image generator 43 with the surgeon actions that are connected through the Surgeon Interface 47 and the mechanical Properties and other modeling that the Host includes that all will reflect the new state that the Host will send to the IG 43 during each simulation cycle.

By eliminating the central server through which all messages pass, ST-DIS dramatically reduces the time lag for one simulator (computer) to send important information to another simulator (computer). This time lag, known as latency, can, if too large, seriously reduce the realism, and therefore the effectiveness, of a networked simulator. Effective distributed simulation depends on very low latency between the times a new state/event occurs for a simulated entity to the time the state/event is perceived by another entity that must react to it. Any delay introduced by the training device results in the negative reinforcement to the operator (e.g., the surgeon).

According to the recommended practice for communications architecture (IEEE 1278.2), the underlying communications structure should support 100 ms or less latency for packet exchange for closely coupled interactions between simulated entities in real-time (e.g. simulating high performance aircraft in a dogfight or simulating a surgeon performing brain surgery). This requirement is based on human reaction times that have been the basis of Human-In-The-Loop (HITL) flight simulator designs for many years.

Within the ST-DIS system, the virtual world is modeled as a set of Entities (as described previously) that interact with each other by means of events that they cause. An Entity is a sub-component in the simulated scenario, such as tissue, specific characteristics (such as—tissue mechanical properties,) creating a sub group of that "tissue entity". Another Entity can be a blood vessel, for example, and so on. Each Entity can have several subEntities that operate in a distributed manner (such as on different simulators/computers). Together, those subEntities are combined to create the complete Entity model. Those subEntities are, for example: the Visual subEntity that holds and simulates the Entity's visual feature and characteristics, or, the Mechanical Properties subEntity that holds and simulates the Entity's mechanical feature and characteristics. Each of those subEntities model code can run in a different computer (or group of computers) such as a PC, and they communicate with each other as well as with other Entities via the ST-DIS network. The simulator nodes, independently simulate the activities of one or more Entities (or subEntities) in the virtual world of the simulation and report their attributes and actions of interest to other simulator nodes via messages on the ST-DIS network. The other simulator nodes on the network are responsible for "listening" to the network messages, determining which ones are of interest to them (based on the entities they are simulating) and responding appropriately.

The above-described Surgical Theater architecture is based on this Distributed Simulation concept thereby enabling pioneer and exclusive abilities to deliver a premier fidelity which is an essential requirement for creating immersive scenarios crucial for the rehearsing of open/classic surgeries where the surgeon(s) interacts with the organ(s) by direct human sense. As each Entity is divided to its sub-components (visual, mechanical properties and so on), and as each of those subcomponents/Entities' simulation code runs in a separate computer, this can maximize the computation power, and by that the creation of a unique and exclusive premier fidelity, fine cues, and computing capabilities while handling terabytes of information under hard "real-time" constraints while maintaining real time performance (e.g., less than 100 millisecond latency), the core capability of the Flight Simulation technology.

The Surgical Theater facilitated a visual rendering engine which analyzes 3D MRI and CT patient-specific images and creates computerized segmented modules that represents anatomical structures and features of the particular image. Medical market has a vast number of advanced DICOM viewers, but as magnificent as those captured images or moving sequences might be, they are based on a fixed set of snapshots in time. The Surgical Theater takes existing 3D model conversion algorithms and adds the features specific of the human tissues and strictures based on physical and mechanical properties creating a "living" image with models that reforms the patient specific CT/MRI images according to actions taken by the surgeon and based on the models that simulate the mechanical properties of each pixels in the image and realistic visual characteristics models. Once this patient-based model is set in motion in the virtual world, a set of virtual surgical tools (that can include aneurysm clips and clip appliers, implants such as bone joint implants, or other devices) are introduced allowing the surgeon to manipulate (push, cut and etc.) those models similar to a real surgery tissue manipulation. Thus, the Surgical Theater provides an intuitive experience for the user.

For the Image Generator, the Surgical Theater of the example embodiment integrates a proprietary Flight Simulation Image Generator algorithm with a visualization code such as Visualization Tool Kit (VTK). As detailed in the following sections, the Surgical Theater Realistic Image Generator has features that deliver fine cues such as shadowing, texture, and material properties that are assigned to the visual models.

The Realistic Visual Sub System

This section focuses on the "realistic visual" segment of the Surgical Theater that is a modification of a Flight Simulation Image Generator that is capable of rendering satellite images into realistic 3 dimensional images and models that are converted into the Surgical Theater realistic Image Generator (RIG) handling and real time rendering CT/MRI DICOM images into a patients' specific realistic and dynamic CT/MRI images and models that are crucial for the open/classic surgeries where the surgeons interact with the organ by direct human sense.

The use of a visual system in the creation of the immersive simulation system in the field of Human factor Engineering is important; studies demonstrate that a high percentage of the immersion is constructed and contributed by the level of fidelity and realism of the visual system that the operator (e.g., pilot or surgeon) interacts with. Findings show that operators who rehearse on high fidelity visual systems completed the memory task including self-report of confidence and awareness states in significantly higher levels than the low fidelity group. A significant positive correlation between correct 'remember' and 'know' responses, and in confidence scores, are found when utilizing high fidelity, realistic simulation.

As outlined above, the Surgical Theater creates a realistic "life-like" digital rendition of the surgical site and the surrounding tissues/structures. Since this digital rendition is patient-specific and "life-like", it sets Surgical Theater apart from other simulators that use generic imagery to create approximate renditions of the surgical site, or, other system that simulates noninvasive procedures such as endoscopic, vascular and similar procedures, where the surgeon/operator interfaces the organism with a camera that has its own visual characteristics that are defined and limited by the camera specification and are very different from the visual characteristics of the bare and direct eyes view of the open/classic surgeon's where the surgeon interacts with the organism with direct sense of his eyes However, realistic "life-like" rendering presents a surmountable task due to the complexity of the properties of the living biological tissues. In order to create such high degree of realism, the Surgical Theater includes a Real Image Generator add-on (RIG): a visual system where patient-specific images of the surgical site, together with surrounding tissues, is realistically presented and can be manipulated in this all-purpose manner.

Figure 5:
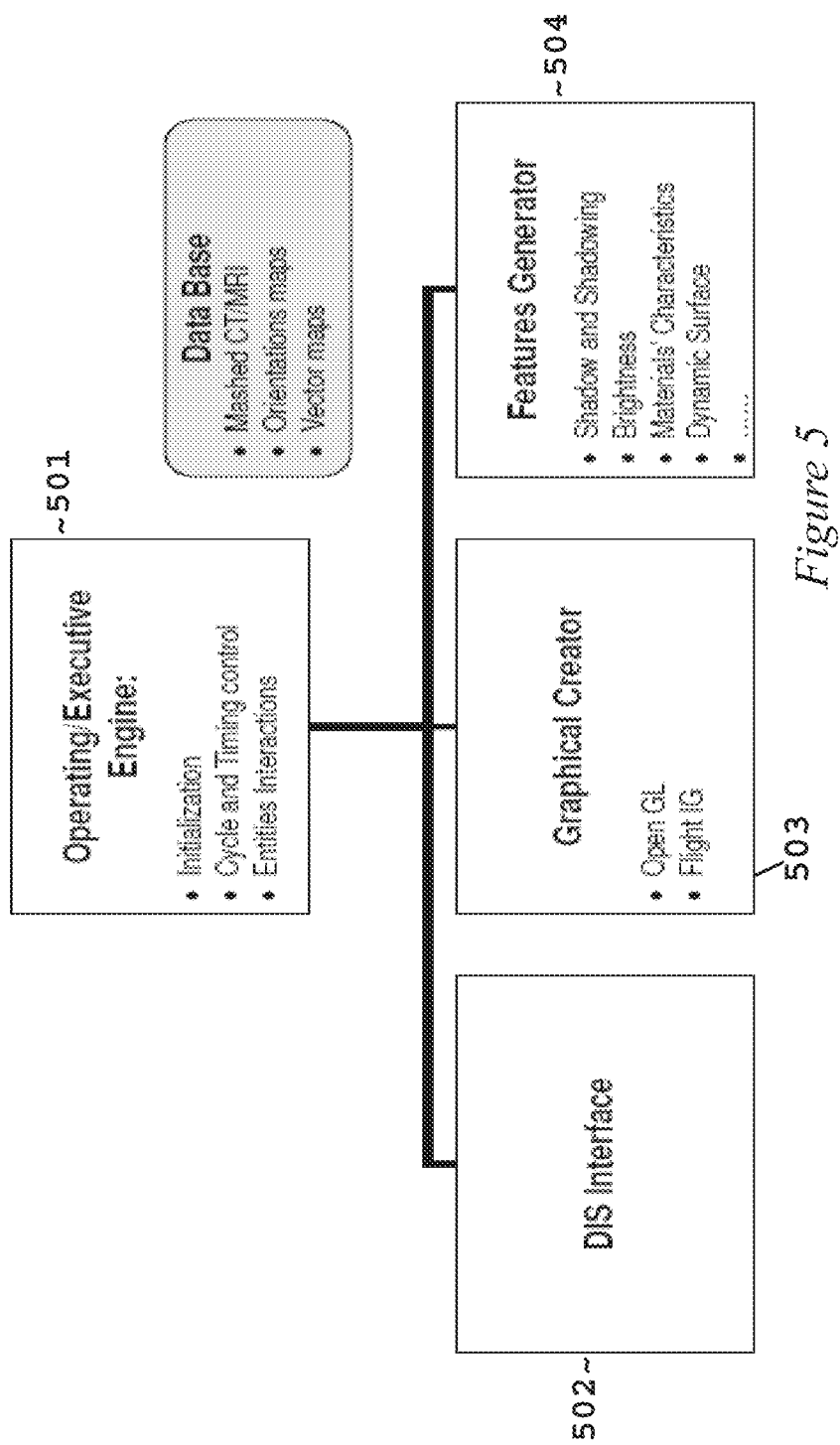
FIG. 5 provides an example high-level Realistic Image Generator (RIG) platform for the Surgical Theater.
Figure 6:
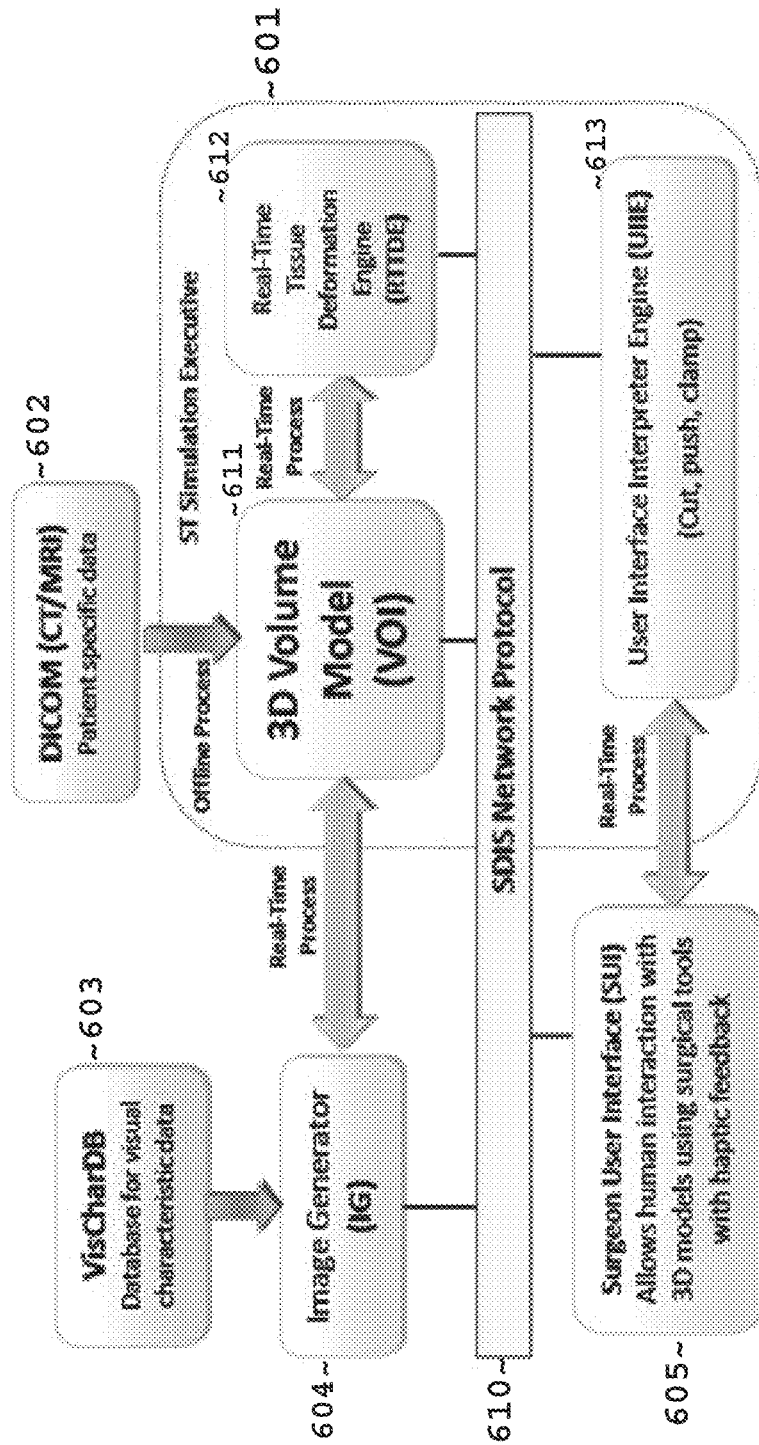
FIG. 6 provides an example high-level architecture and workflow of a Surgery Rehearsal Platform (SRP) for the Surgical Theater.
Figure 7:
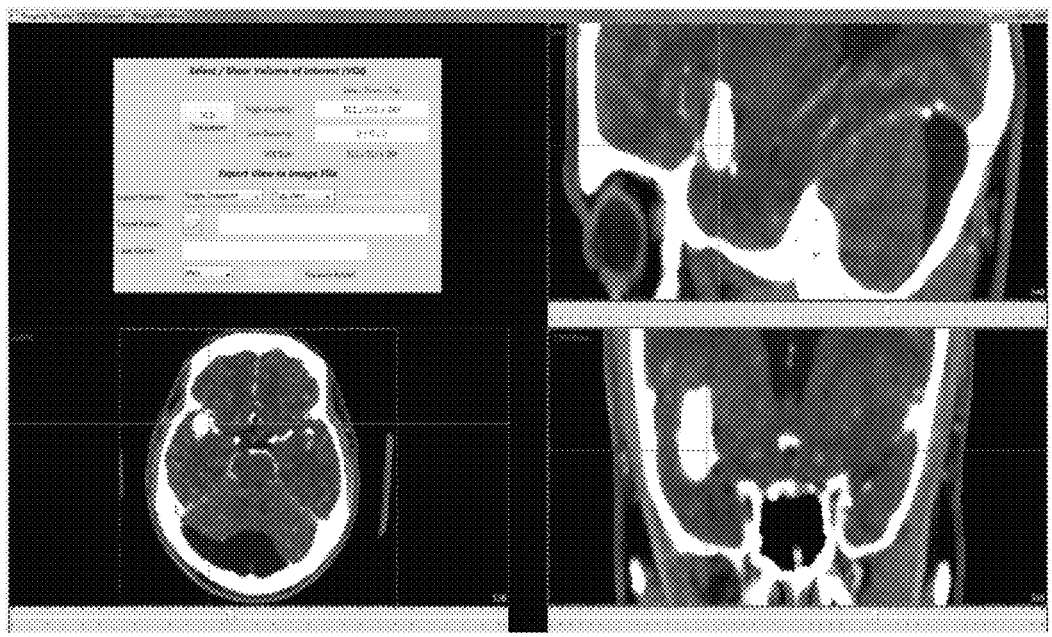
FIGS. 7-8 and 8A are example screen shots of windows in a DICOM Volume Viewer example for the Surgical Theater.
Figure 8:
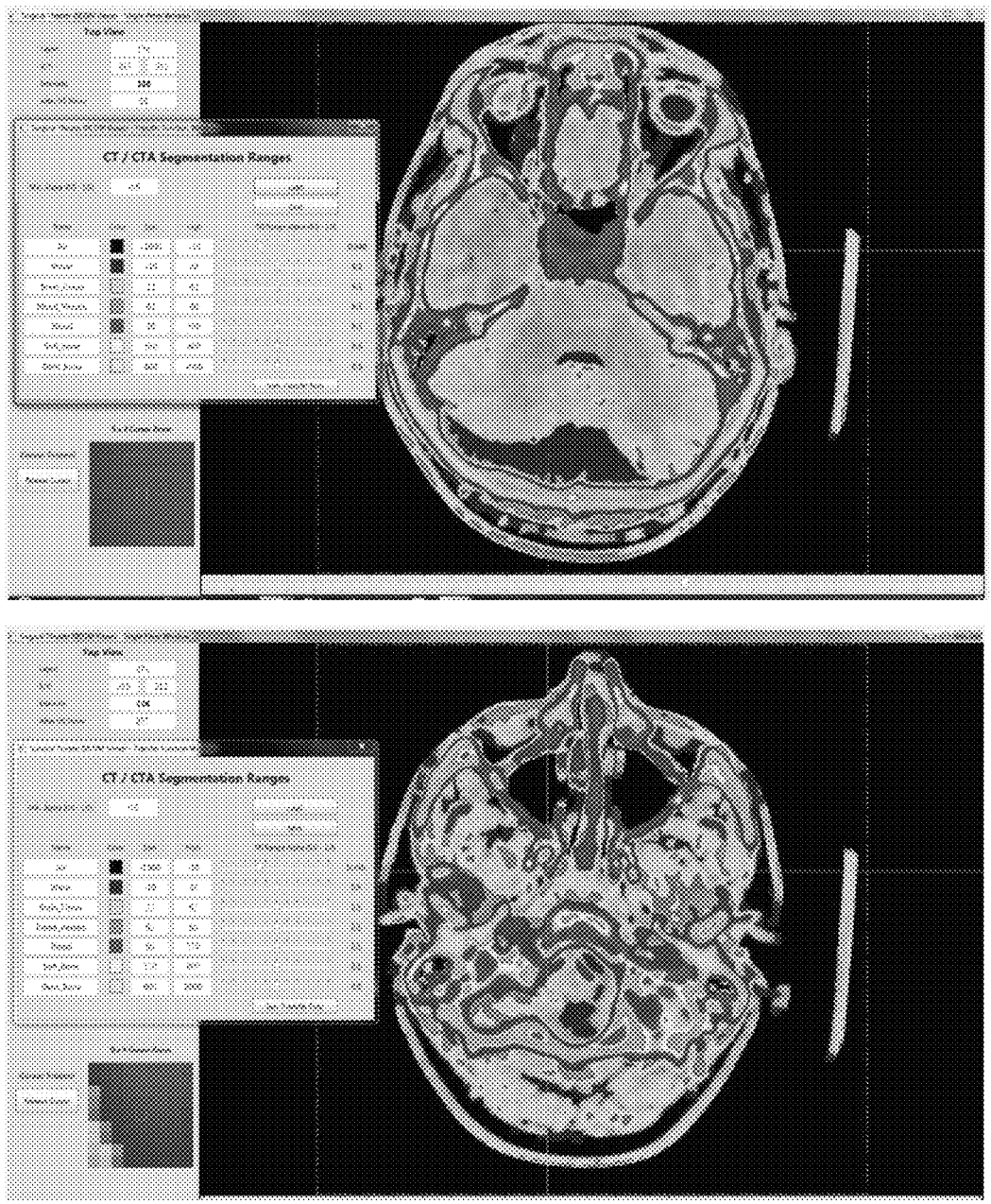
Figure 8A:
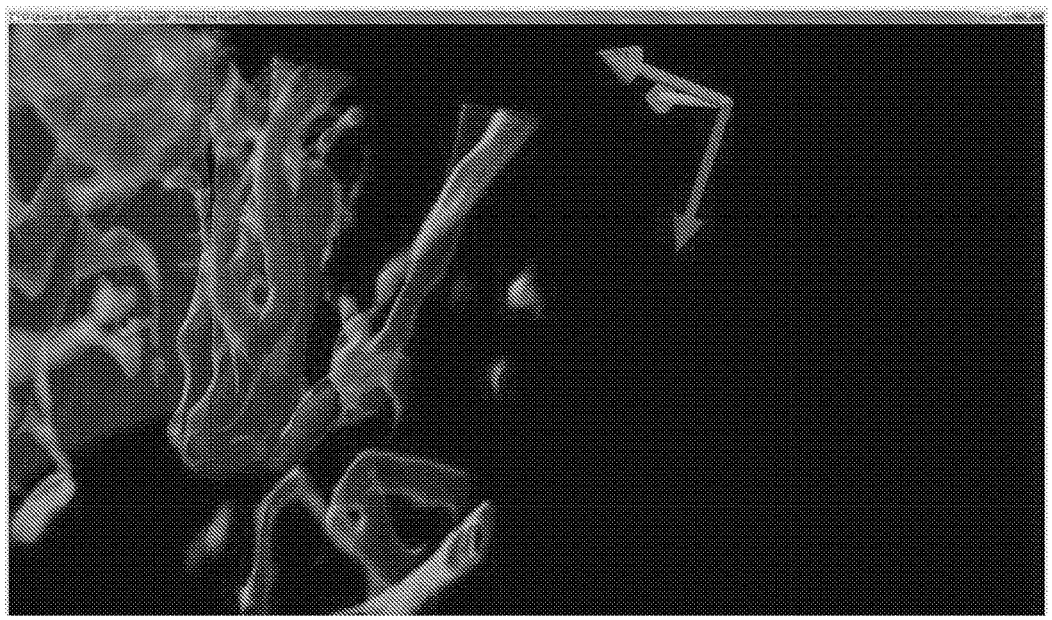

FIG. 5 shows a RIG Architecture Block Diagram. Data Base box—collection of the mesh modules based on the patient-specific CT/MRI, 3D and segmented images, preprocessing of the images, smoothing, masking, scaling. Graphic Creator box—Interface to the graphics card. ST-DIS Interface box—Interface to the ST-DIS network. The figure shows a hierarchy diagram of the visual systems. The system includes an executive program that runs and manages all the system components and updates the statutes of the sub components according to the surgeon/operator and the status of all the sub components as they are read through the DIS network (502). The Operating/Executive Engine (501) is responsible for the initialization of all the software and hardware components in a way that all the system's components are working with the same data bases (for example, the set of tolls that the surgeon choose). When the scenario starts, the Operating/Executive Engine (502) performs the cycle and timing control and perform the task of managing each component to complete its calculation cycle within the time frame that it is planned on in a way that all the system's sub components receive the information from the other sub components on a timely manner allowing the overall system to complete the simulation cycle in a given time frame. For example, when an action is taken by the surgeon and transmitted by the DIS network (502), the Feature Generator (504) reads the relevant part of this action/consequence of this action as calculated by the mechanical properties algorithm, the Graphic Creator (503) change the image according to this action (for example, move a vessels that was pushed by the surgeon), then calculates the changes that need to be applied on the image as a result of this change, for example, creating a shadow resulted by the change of the vessel location and orientation. This cycle is executed rapidly and continuously managed by the Operating/Executive Engine (501) in a cyclic manner in a way that each cycle is completed within a frame time of milliseconds allowing the surgeon/operator to receive real time and realistic cues.

CA-SRP General Description:

The Surgical Theater concept can be adapted to support the CA-SRP Process. CA-SRP converts a patient specific CT and MRI imageries and creates a realistic three dimensional (3-D) model of the aneurysm area with a dynamic modeling of the organisms, including the surrounding tissue and blood vessels. The CA-SRP is connected to real surgery tools (including any real surgical device that can be manipulated by the surgeon and interfaced to the CA-SRP) in a way that the handles of the user interface that the surgeon works within the CA-SRP are similar to the ones that he holds in the surgery, responding to actions taken by the surgeon, helping him/her to better prepare for the surgery. The CA-SRP system simulates realistic events such as brain swelling, damage to blood vessels, brain tissue shifting during an operation that blocks the surgeon's access to the area he planned to access, as well as other complications such as; (i) Inappropriate temporary clip placement will not stop the flow of blood into the aneurysm, (ii) Improper management of the aneurysm will result in bleeding if temporary clips were not placed or not sufficiently placed (iii) If the temporary clips were on for a long time a feedback of possible stroke will be generated (iv) If the aneurysm clip will obstruct a vessel coming out of the aneurysm or is attaching at the aneurysm neck, a stroked patient outcome will be reported.

CA-SRP Cerebral Aneurysm Surgical Rehearsal Platform (CA-SRP) is centered around a software simulation engine, based on state of the art algorithms for segmentation, soft tissue and collision detection algorithms that calculate orientation interaction between all the elements and detects when an interaction occurs (such as the surgery tool touching a tissue or vessel). This interaction information (location, angels and so on) is populated to the models of the tissue for calculating the tissue deformation due to this interaction a s well as to the surgery tool to provide force feedback to the surgeon hand due to this interaction. The area of interest (i.e. Aneurysm) is presented to the surgeon on the workstation, using a high fidelity visual; real-time, real 3D (stereoscopic visual) and realistic (life like visual— texture, shadowing, shininess) image generator that presents both the organ as well as the surgery tools being used by the surgeon.

Aneurysm repair surgery is extremely time-sensitive due to various procedures such as temporary vessel clamping in which the blood flow toward the aneurysm area is blocked. The time-efficiency of the procedure is highly critical and detailed planning based on the local, patient specific geometry and physical properties are fundamental and will result with an enhanced clinical outcome and a better operational efficiency. Surgical Theater is allowing surgeons to obtain critical insights for refining the surgery strategy and enhancing the surgery outcomes.

CA-SRP Architecture:

The CA-SRP realistic behavior of deformable tissue modeling is utilizing Finite Element Methods (FEM) using mass lumping to produce a diagonal mass matrix that allows real time computation. Additionally, it utilizes an adaptive meshing that is necessary to provide sufficient detail where required while minimizing unnecessary computation.

The CA-SRP's brain tissues modeling is based on published studies of this area, for example, studies may include the followings, yet, CA-SRP can adopt any description of tissues' mechanical properties: i) Miller K and Chinzei K. Mechanical properties of brain tissue in tension. J Biomech 35: 483-490, 2002, and, ii) Miller K, Chinzei K, Orssengo G and Bednarz P. Mechanical properties of brain tissue in-vivo: experiment and computer simulation. J Biomech 33: 1369-1376, 2000, both incorporated herein by reference.

CA-SRP design employs patient specific data, CT and MRI imageries that are converted to a 3D soft tissue model using our above described algorithm. This algorithm uses image enhancing processing and segmentation methods to create a high fidelity segmented model that presented to the surgeon and react to the surgeon actions. The 3D soft tissue model is then handled in real time by our STDE (Soft Tissue Deformation Engine) that uses tissue properties from the mechanical properties studies. Other inputs to the STDE include the User Interface (UI) tools used by the surgeon and the resulting actions on the model. The resulting deformed model is fed into a high fidelity image generator that displays the model in a realistic way to the surgeon.

The CA-SRP code runs in Windows platforms coded using standard development tools, utilizing available software packages such as .NET, WPF, OpenGL and available simulation frameworks such as SOFA and GiPSi. The information shared between the different modules of the simulation, is distributed using a proprietary protocol; the Surgical Distributed Interactive Simulation (SDIS) which is based on the Flight Simulation "Distributed Interactive Simulation—DIS" protocol, and which can be adapted from the Surgical Theater concept introduced above. The SDIS core idea is to minimize the amount of data needed to be shared and therefore, allowing real-time performance with scalability and independence of the different distributed system components that execute separate portion of the simulation (i.e. visual, mechanical properties).

SDIS Based Architecture:

The SDIS based architecture facilitates a unique and exclusive ability for premier fidelity, fine cues and computing capabilities while handling large volume of information under hard real-time constraints while maintaining real time performance which is the core capability of the Flight Simulation technology. One of the features of the SDIS network is that there is no central server or processor, each simulation node (nodes may be: Image Generator, User Interface, Mechanical Modeling computer and so on) maintains its own copy of the common virtual environment— vessels, tissues and other models that are held and maintained at each of the simulation node; each such model is handles as a separate "Entity". This architecture enables several PCs to work together in a synchronized manner under hard real time constraints allowing CA-SRP's pioneering and unique capabilities to deliver a premier fidelity of the simulated scene. This creates an immersive scenario that allows rehearsal of open/classic surgeries where the surgeons interact with the organ by direct human sense.

Once the surgery tools and the other Entities are selected by the surgeon, they are integrated into the virtual surgery scene and turn into an integrated element of the simulated scenario including realistic visuals features and mechanical properties and operation properties features that are applied to each one of those selected items, for example—the scissors have the real mechanical characteristics and will cut as the real scissors do, and, Aneurysm clips, when placed at the vessel, blocks the blood flow.

Figure 9:
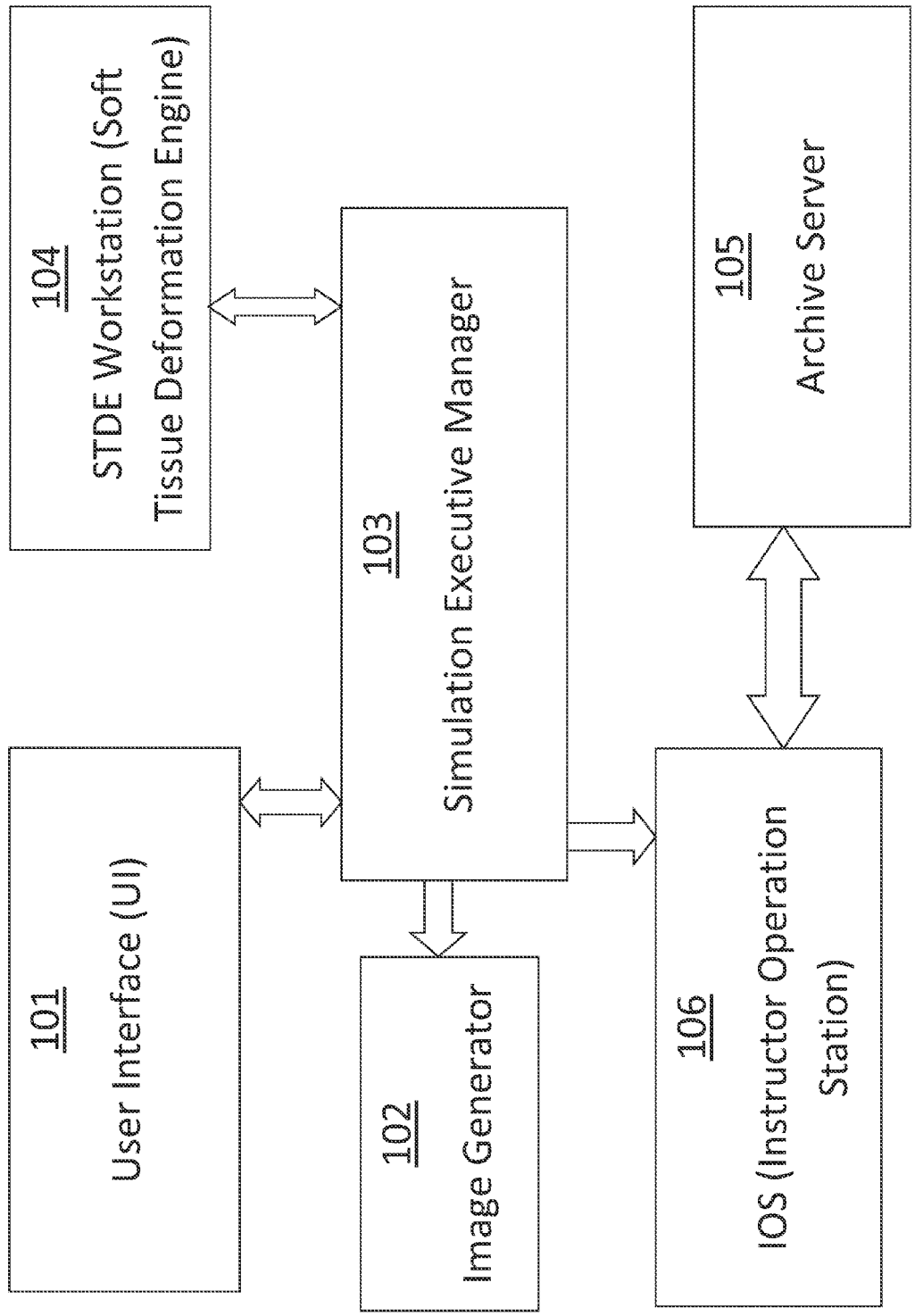
FIG. 9 shows a high-level block diagram of an example embodiment of the Cerebral Aneurysm Surgery Rehearsal Platform (CA-SRP)

The CA-SRP system as is compose by the following units or combination of sub parts of the units depended on the configuration, volume that needs to be simulated and the specific application. These are similar to those for the Surgical Theater system as shown in FIG. 4, but modified as described in this section. The sup components can run in Several separated Computing Processor Units in multiple PCs (FIG. 9):

The workstation that the surgeon works on is the User Interface 101. The Image Generator 102 operates similarly to the like device in the Surgical Theater. The Simulation Executive Manager 103—synchronizes the real time operation of the system, runs, and executes the modeling programs. The STDE Workstation 104—This PC handles the STDE (Soft Tissue Deformation Engine). The Archive Server 105—This station holds all the relevant files and data and able to record the procedure for future debriefing and data collection, and this PC also serves as the network domain controller. The IOS (Instructor Operation Station) 106 is for monitoring and controlling the training session, also allowing the instructor to "inject" events. Also serve as the "Master of Ceremony" and will activate the whole training session.

Each of these Computing Processor Units connects via the SDIS network with a network switch (not shown).

Scenarios of Operation

Figure 10A:
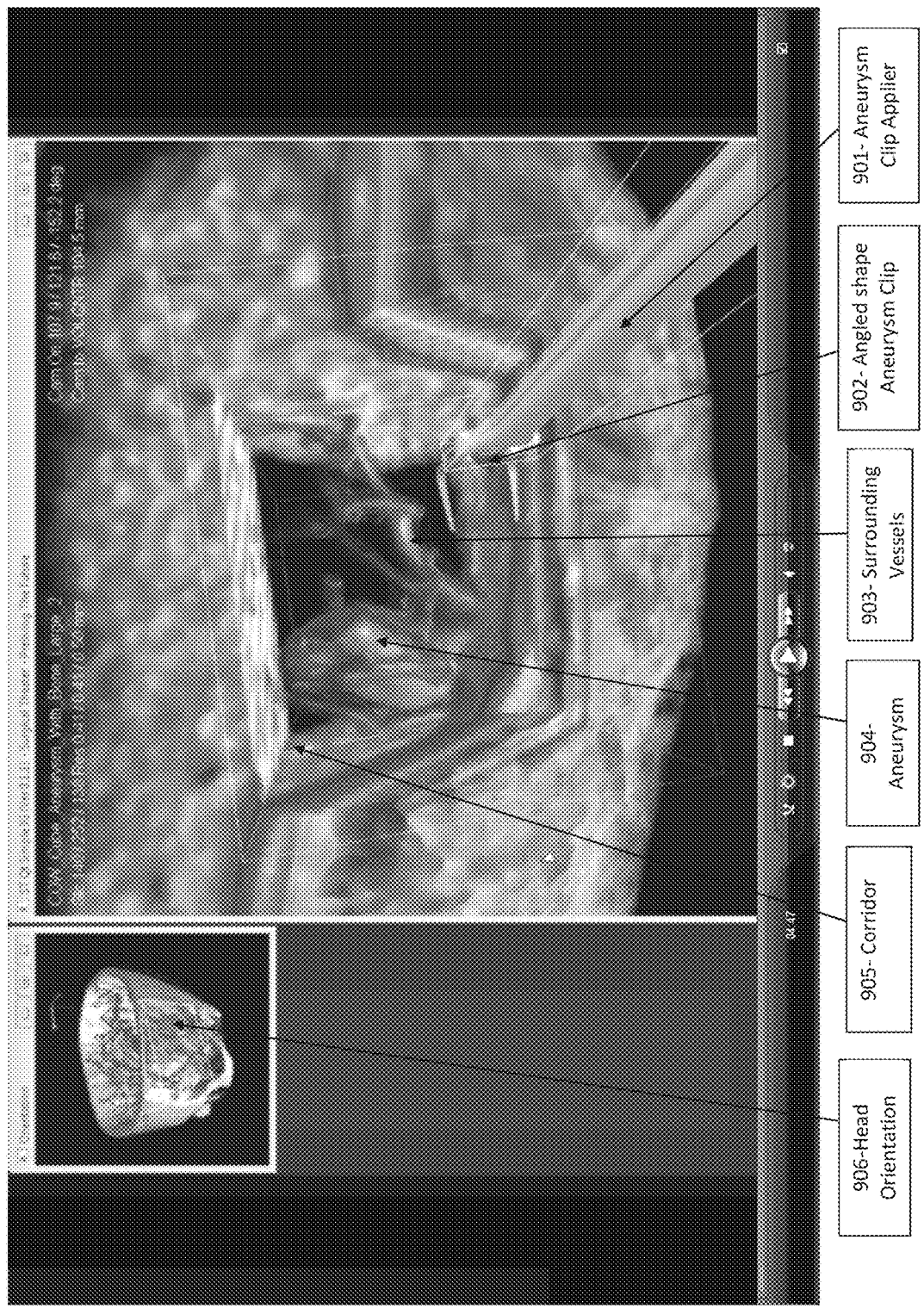

The surgeon uses the CA-SRP to virtually position the head of the patient, to determine the exposure of scalp, craniotomy site and size, and brain retraction to achieve the desired vessel exposure in the corridor 905 shown in FIG. 10A. This part is done in the using the UI simulated operating tools as well as with computer mouse and keyboard. The CA-SRP covers the stages of craniotomy, dura opening, and splitting of the fissure the vessel exposure through temporary clamping through the Aneurysm clip application and removal of temporary clips.

Typical Scenario of Operation: Typical Initial Setup

The surgeon feeds the set-up parameters of his patient which include details of the patient that allow the system to up-load the relevant data, the CA-SRP then loads the patient's CT, CTA, MRI and MRA imageries and other information that concern the simulated models such as patient age, gender and so on.

3 dimensional imagery of a portion patient head is presented at 906 in FIG. 10A; The surgeon positions the head in a desired orientation at 906 (Head Orientation).

Similarly to the actual surgery, the surgeon virtually creates the corridor 905 to approach the aneurysm by virtually removing the tissues all the way to the aneurysm site with the UI. The surgeon marks the area of the site of interest/Aneurysms 904.

The system preferably automatically performs segmentation process and identifies the "Entities"; Entities are vessels, tissues, and so on 903, although manual segmentation can also be provided for. This is done efficiently because of the arrangement of hardware and software that utilizes the parallel processing features of the system, greatly improving system performance in contrast with manual simulations.

"Start Simulation" is initiated: The brain tissues that were "removed" in the initialization process virtually retract back to expose the area containing the abnormal vessel formation. The system then applies, at the marked area of the site of interest/Aneurysms, the layers of the tissues mechanical properties and the realistic visual, and load other relevant parameters and characteristics relevant to the case, all applied on the top of the CT and MRI and synchronized with those imageries. The synchronization creates, for example, vessel mechanical properties that are 'attached' to the vessel imageries. Surgery tools (which may include aneurysm clips, surgical implants, and other devices) libraries are included in the virtual scenario and available for the surgeon.

The surgeon has the ability to "fine tune" the models and adjust the modeling parameters of the simulation by changing the mechanical properties of a certain area of the organ; for example, the surgeon may adjust the elasticity and other mechanical characteristics of the Entities behavior to better match the mechanical behavior of the tissue based on his experience and his anticipation, such as at the Angled shape Aneurysm Clip 902 and the Aneurysm Clip Applier 901 to impact tool and tissue interactions.

Consequently, the CA-SRP efficiently projects the 3 dimensional organ model presented in a realistic visual fidelity with realism features of: texture, shadowing and other features that adds realism to the original image. Each segment of the visual model is coordinated and corresponding with appropriate mechanical properties models.

FIG. 10B shows additional views of the simulation, further showing an aneurysm clip applier 912 after it was used to apply a straight clip 911 on a vessel, and an angled clip 910 on a vessel.

Figure 14:
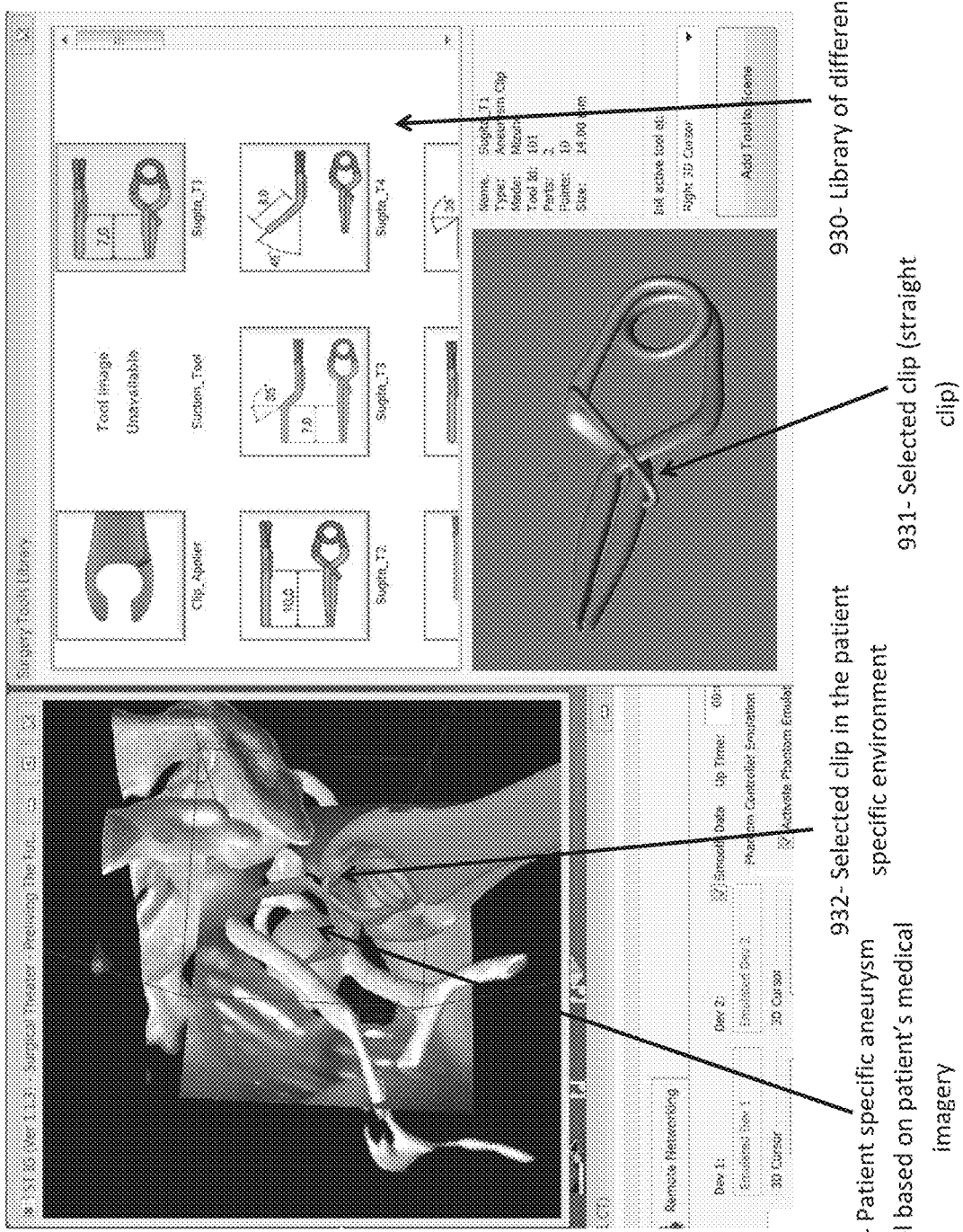
FIG. 14 shows a screen shot of an example aneurysm clip model library and simulation display for the example CA-SRP.

Typical Scenarios of Use:

The surgeon browses and chooses from the system's virtual libraries the relevant surgery tools and other elements (in the system software terms those elements are "Entities" as well) those Entities may include; scissors, bi-polar electro-cautery, suction tips, and clamps, clip applier as well as a variety of Aneurysm clips 930, as shown in FIG. 14, which also shows a patient specific aneurysm model 933 based on the specific patient's medical imagery and the selected clip 932 in the patient specific environment.

Similarly to the actual surgery, the surgeon virtually dissects the aneurysm away from the tissue and the feeding vessels and exposes the neck to receive the clip/vessels and tissue retract or extract per the appropriate mechanical properties models and surgeon's actions the surgeon also selects temporary clip from Clips library; the clip is realistically modeled and can be handled by the surgery tools.

Also similarly to the actual surgery, the surgeon virtually places a temporary clip on the feeding vessels in order to isolate it from the normal circulation, and the surgeon selects a clip from Clips library to address various positions, shapes, and sizes of Aneurysms (the library of clips includes the commercial clips', sizes/shapes/lengths of clips). The selected clip model appears in the scenario; the clip is an accurate and realistic model of the real clip and can be handled by the surgery tools.

Figure 15:
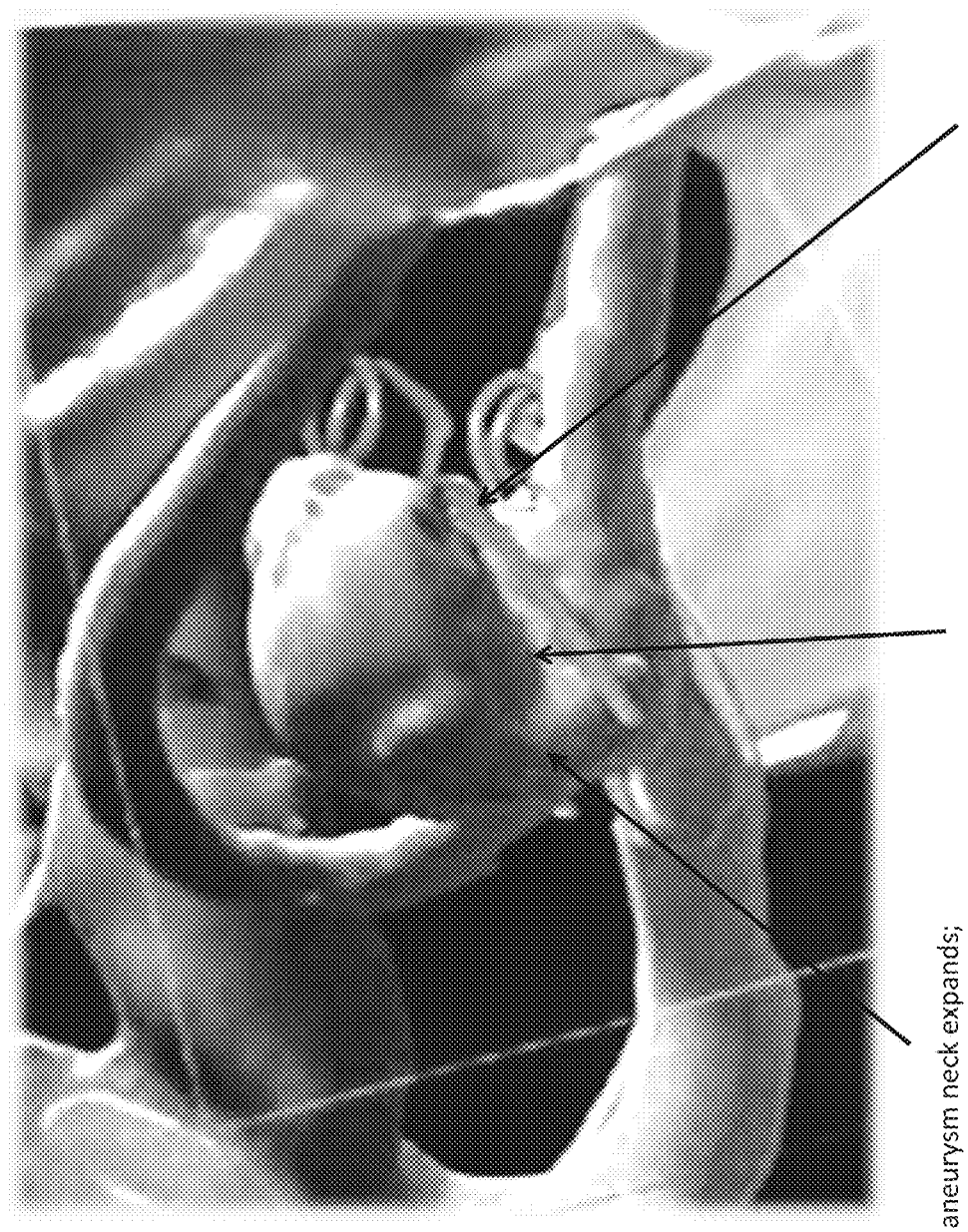
FIG. 15 shows an example 3D simulation display of an aneurysm and aneurysm clip for the example CA-SRP.

Further similar to the actual surgery, the surgeon then virtually places a clip across the neck of the aneurysm. The surgeon rotes the view and look to observe and evaluate the clip placement, as shown in FIG. 15, showing the clip 940 applied on the aneurysm neck. The surgeon can then remove the temporary clips, and puncture the aneurysm. If the aneurysm's neck is not completely occluded, bleeding will occur.

As in real-life surgeries, inappropriate temporary clip placement will not stop the flow of blood into the aneurysm, whereas appropriate clip will cause the aneurysm to deflate or obliterate. Improper management of the aneurysm will result in bleeding if temporary clips were not placed or not sufficiently placed. FIG. 15 shows a situation where the aneurysm neck 941 is squeezed, shrinks and expands 942, indicating that a longer clip may be required. If the temporary clips were on for a long time a feedback of possible stroke will be generated. If the aneurysm clip will obstruct a vessel coming out of the aneurysm or is attaching at the aneurysm neck, a stroked patient outcome will be reported. At any stage of the virtual surgery; the surgeon can "freeze" the simulation and rotate the organ to observe the area of his interest from different orientations and perspectives.

The surgeon is able to "mark point of time" of the virtual surgery and then can command a "return to the mark point"; for example, the surgeon can mark the time before clamping the aneurysm and return to this point of time while "undoing" all the actions that took place after this point of time. In this fashion, the surgeon can evaluate different surgery approaches of a selected phase of the surgery without restarting the entire surgery from the original starting point. Several such 'mark points' will be available allowing the surgeon to return and "re-do" actions and exams/rehearse on several selected phases of the surgery.

CA-SRP will be mainly used as a planning and preparation tool toward a patient specific surgery. Thus, allowing surgeons to tailor a specific surgical strategy for a given case, maximizing the surgery efficacy while minimizing the risk all contributing for an enhanced surgery outcome.

Additional scenarios of the CA-SRP use may include: (1) Surgeon rehearsals toward a surgery; (2) Surgeon demonstration to the chief surgeon; (3) Surgeon peer review and collaborate with colleague that may have CA-SRP through internet or other network connectivity; (4) Surgeon demonstration to a resident; (5) Surgeon researching and developing new method; (6) Resident/fellow practice; (7) Scrub techs/nurses/physician assistants practice will allow them to understand the surgeons role and hence their role in these operations; (8) Platform for development, testing and validation of surgery equipment, tools, or equipment; for example—aneurysm clips, that will be exams in a realistic simulated environment; (9) Surgeon community platform to share knowledge and accrued experience; (10) Platform for resident and surgeon evaluation exams and certification; and (11) Platform to promote the use of specific surgical tool or instrument such aneurysm clip.

CA-SRP allows the surgeon to record his actions and save them for later playback and to demonstrate his surgery plan to the chief surgeon, resident, or, to share information with other surgeons or to demonstrate new techniques he is working on, and so on. CA-SRP's interfaces to the surgeon includes surgery interfaces (i.e. handles) scissors handles, by-polars and bayonet forceps and aneurysm clip applier. Those interfaces may or may not include force/haptic feedback that is delivered to those tools to allow the surgeon to sense the force feedback cue of his actions. Providing force/haptic feedback can be especially useful in providing a realistic simulation, and thus is preferable.

Figure 10C:
Figure 11:
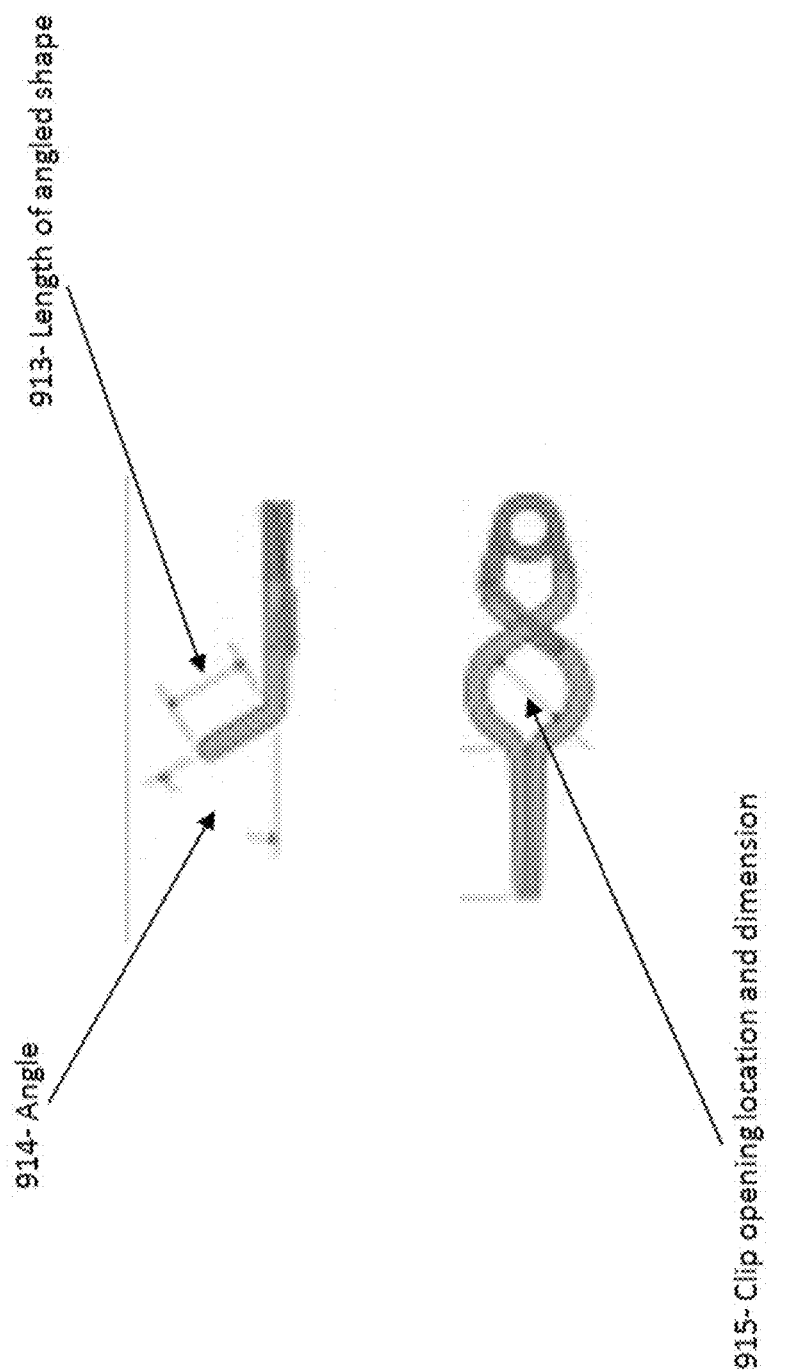
FIG. 11 shows example aneurysm clip model dimensions.

Tailored, patient specific, design of cerebral aneurysm clip: The CA-SRP includes a search engine that allows the surgeon to locate an aneurysm clip that matches the patient specific aneurysm and vessels 3 dimensional geometrical structure. By feeding set of physical parameters such as; overall aneurysm clip length, determination of the aneurysm clip shape (number of angled shapes, sequence and angel values), number of aneurysm clip holes (number of holes, location, sequence and shape/diameter) and other structural characteristics, as shown in FIG. 11, items 913, 914, 915. Additionally, a graphic user interface allows the surgeon the option to work with a 3 dimensional model of an aneurysm clip and to design its own clip to match the patient specific aneurysm and vessels 3 dimensional geometrical structures—when the surgeon completed the design of the aneurysm clip (by either methods) the model of aneurysm clip with the surgeon's design, appears in the CA-SRP. See FIG. 10C showing the Aneurysm Clip Applier 907 applying Straight shape Aneurysm Clip 908 The surgeon then can send the tailored design clip in a 3 dimensional photo file (jpeg, bitmap and comparable) for rapid manufacturing. If a clip that matches the surgeon's input of the above parameters is commercially available, the CA-SRP provides the aneurysm clip manufacturer, part number and the 3 dimensional model of the aneurysm clip appears in the CA-SRP. The surgeon then uses the clip applier to grab and hold the clip, to open the clip against the clip spring while the force of the clip is sensed in the surgeon's hands. The surgeon then maneuvers the clips and applies it, using the clip applier, on a vessels or the aneurysm. The surgeon can repeat this process as many times as he desires with different clips.

This method and platform used to tailor a specific graft shape and design for bypass surgeries, a specific bolt screw or any other implant for spine surgeries, orthopedic implants and many other applications. The platform also supports integration of any medical imagery with surgery tools (such as clips, implants, and other surgical devices) and a user interface and tools for modifying the implants and allowing tailored design to match the implant to the patient specific case based on a dynamic and interactive model.

Case Study Example—Scenario of Operation of a Tailored Made, Patient Specific Design of an Aneurysm Clip:

The surgeon/operator starts with one of the available baseline clip models that the surgeon selects from a library 930, such as shown in FIG. 14. The surgeon/operator then evaluates the clip on dynamic and interactive model of a patient specific (based on medical imagery such as CT, MR, X-ray, Ultrasound and others) as shown in FIG. 15 and discussed above.

Figure 16:
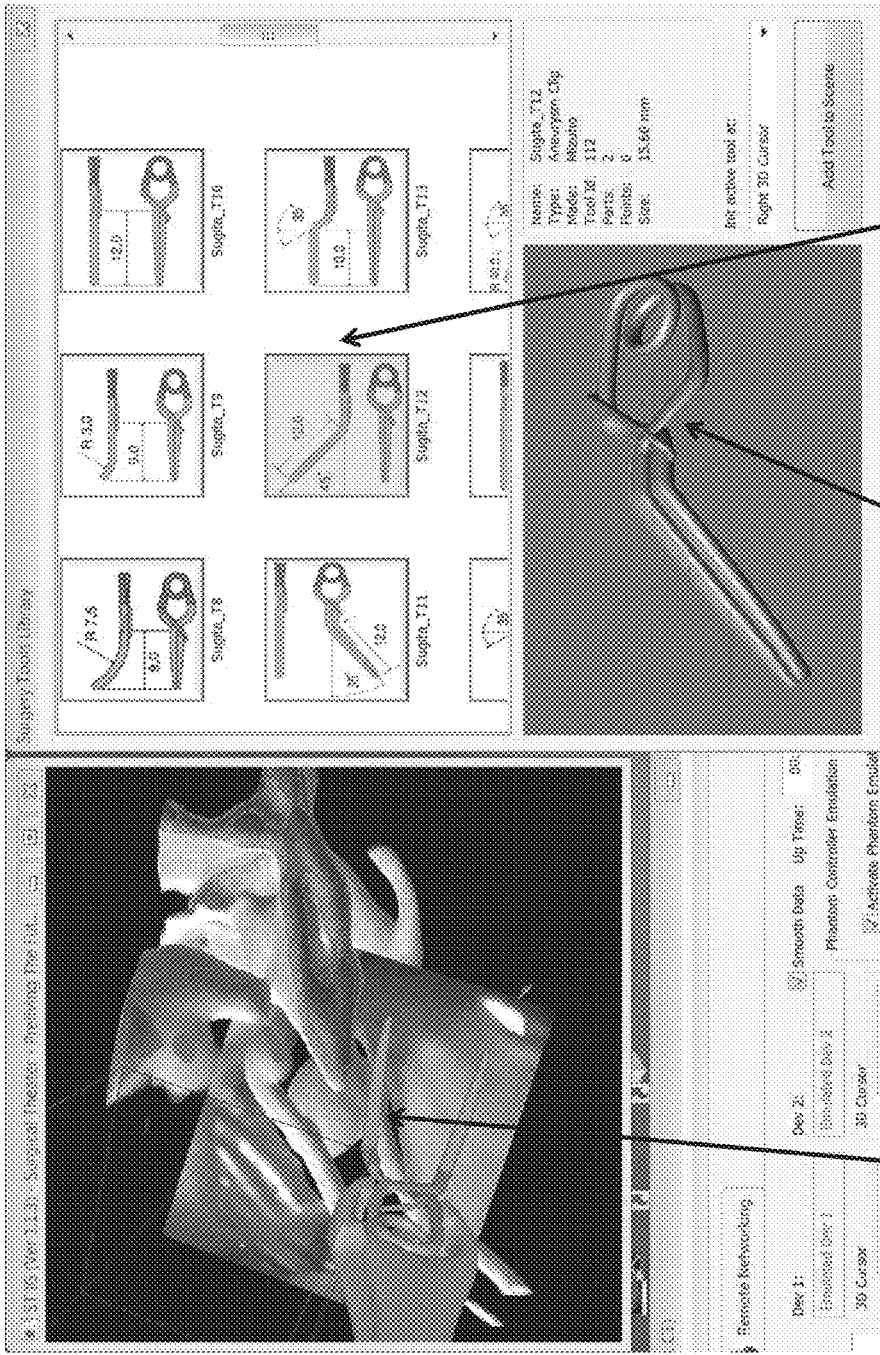
FIG. 16 shows a screen shot of an interface for selecting example aneurysm clip models from a library.
Figure 18:
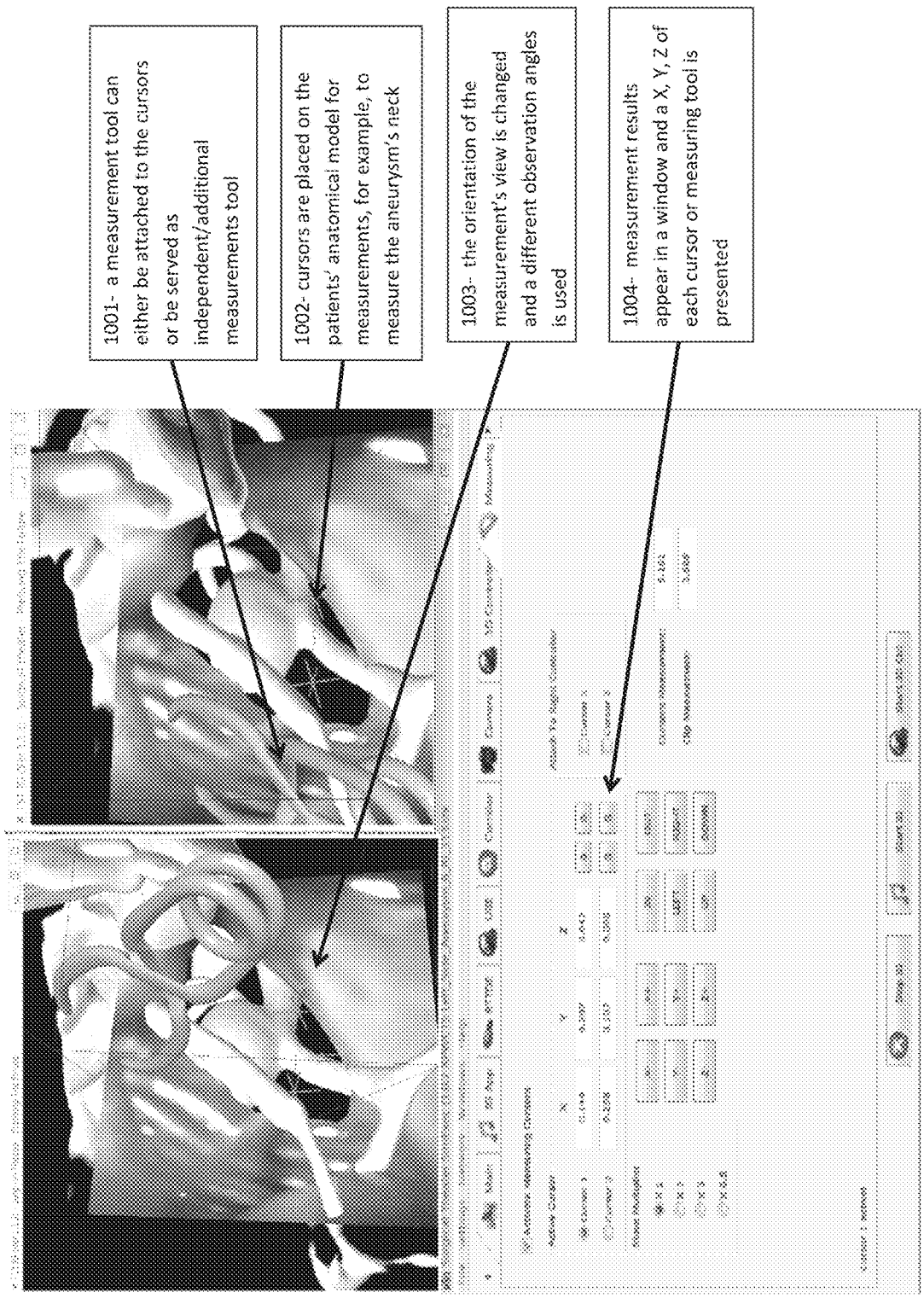
FIG. 18 shows a screen shot of a surgeon interface for performing measurements of an aneurysm neck before and after applying the clip for the example CA-SRP.

The aneurysm shape is changed due to the dynamic nature of the modeling—the clip pressure on the aneurysm tissue cusses squeeze and reshape/expansion of the aneurysm neck, as shown at 941, 9421$n$ case that the evaluations on a patient specific subject determine that the selected clip is not sufficient (does not exclude the entire aneurysm or create stress on the surgeon gong vested and others . . . ) the surgeon/operator can choose different clips for evaluations from a library 950, as shown in FIG. 16, where the surgeon is shown selecting a new curved clip 951 for applying to the patient specific aneurysm 952. The surgeon/operator can perform measurements of the aneurysm neck before and after applying the clip, as shown in FIG. 18, where a measurement tool can either be attached to the cursors or be served as independent/additional measurements tool 1001; the cursors are placed on the patients' anatomical model for measurements 1002, for example, to measure the aneurysm's neck; the orientation of the measurement's view is changed and a different observation angles is used 1003; and measurement results appear in a window and a X, Y, Z of each cursor or measuring tool is presented 1004.

Figure 17:
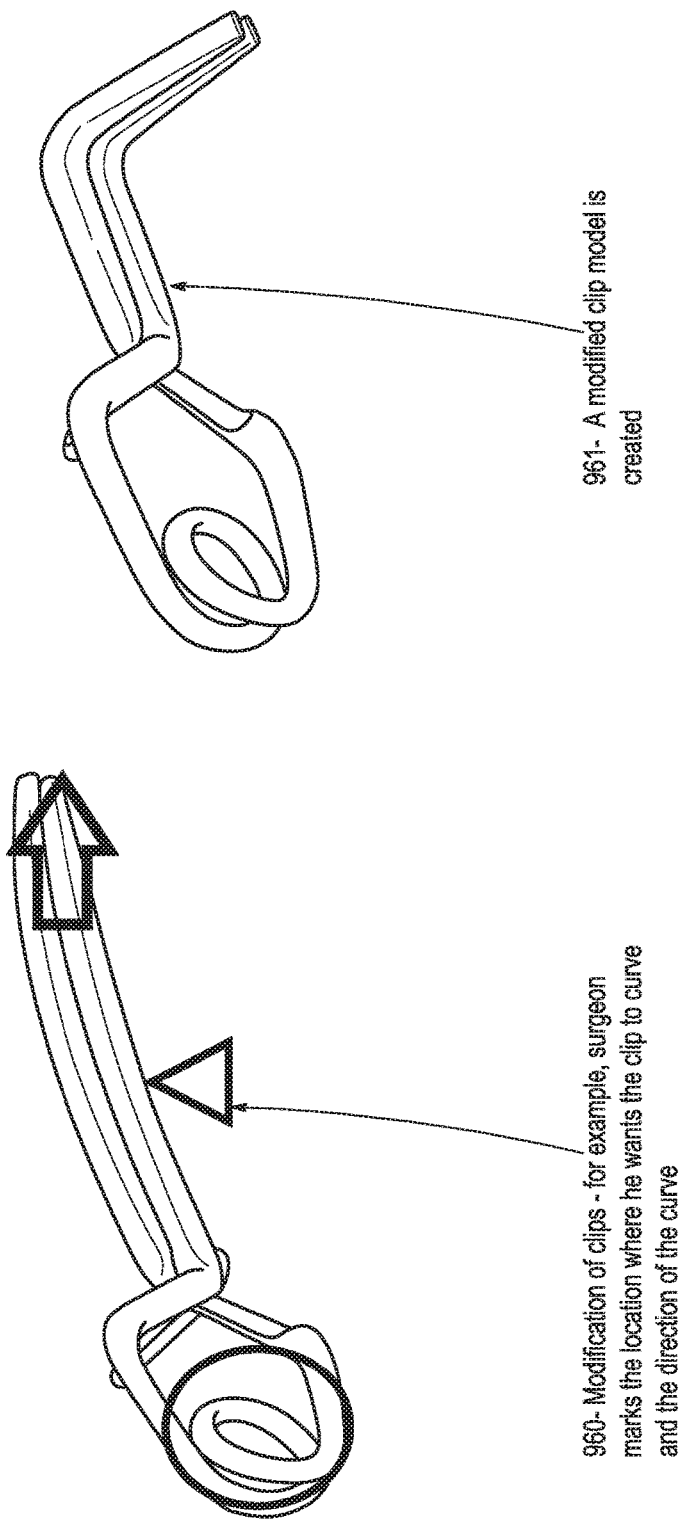
FIG. 17 shows an example display of aneurysm clip modification for the example CA-SRP.

The surgeon/operator can change length, shape, Angles and so on to create a tailored, specific clip design that is the best fit for the specific patient, as shown in FIG. 17, with a modification from clip 960 to clip 961. The surgeon/operator can define areas that he would want to get several options of clips (for example—clips with overall length of length, 10, 15 and 17 millimeter or angle of curves of 15, 20 and 25 degrees and so on). A 3D model is created for manufacturing of the clip as shown in FIG. 17. Hence, a tailored made clip designed specifically to match the patient's own anatomy based on the simulation results can be manufactured and sent to the surgeon to be used and to be applied in the actual surgery. Similarly, other surgical tools and implants could be customized in a like manner, by first testing their operation via simulation. This can be used to improve surgical results in a manner not available without simulating the surgery in advance.

In the patient specific modeled simulated environment that is built on the foundation of the patient's medical imagery (CT, MR, X-ray, Ultrasound etc.) the surgeon: (1) creates the corridor by removing and shifting tissue to expose the targeted site (aneurysm, faulty vessel, faulty heat valve, fractured bone, damaged knee, damaged hip, damaged shoulder and so on). (2)—the simulated environment is segmented and includes: bone, soft tissue, vessels, nerves etc. Therefore the corridor that is created is realistic and accurately represents the limited approach to the that will be available to the surgeon in real surgery and it will take into consideration the anatomical obstacles (for example, eye tunnel bone that block the approach to an aneurysm that needs to be removed). (3) when the site that needs to be treated is exposed, the limited available approach and the orientation of the approach represent the realistic limited work environment that the surgeon will face in the operating room. (4) the surgeon browse the Surgery Rehearsal Platform (SRP) implants library and select a commercially available implant to try or, a generic model—both are provided with the option for modifications. (5) the surgeon remove and dissect any anatomical structure that needs to be replaced (i.e. faulty heart valve or faulty knee) (6) the surgeon maneuver the new implant through the corridor with the realistic limited space available. (7) the surgeon places and attached/apply the implant on the treated site. (8) the simulated placement takes into consideration and it based on the patient's anatomical structure such as; thickness of the bone available for attaching the implant (artificial knee, artificial shoulder, artificial hip etc.) and/or thickness of the vessel available for attaching the implant (bypass graft, artificial heart valve etc.), the dimension and orientation and the implant site etc. (9) a 3 dimension design tool allows the surgeons to adjust modeling parameters of the simulation to modify the implant (or other implantable device) to better fit the patient's specific anatomy—for example, the length and angels of an aneurysm clip can be modify in order to create a tailored designed clip that will best fit the patient's specific aneurysm's size and shape and the specific orientation of the approach/corridor to the aneurysm. Other example may be modification of the dimension of the round or oval heart valve to better match a patient's own anatomy. Additional example may be the tailored design of the thickness, shape and length of a plate that is placed to treat a broken bone. Other examples of adjusting modeling parameters may be a tailored design of a graft to treat bypass or aneurysm, a tailored design and shape and angles of the artificial knee, artificial shoulder, and artificial hip. (10) the SRP and the modeled artificial implant support the performances of adjustments and alignments needed for the implant, for example aligning bands and strips of a knee that being done in the operating room—the SRP allows the performance of this alignments in advanced in the simulated environment. For example, the lengths of the bands and strips of a knee can be pre-detainment in the SRP/simulated environment before the surgery start. (11) once the surgeon complete the design, he commend the SRP to create a "manufacturing model"—a file with the 3 dimension model with accurate dimensions (length, thickness, angel and so on) all based on the surgeon's tailored design. (12) instruction for pre-alignments is created, for example, instructions for alignments of the bands and strips of a knee. (13) a file or a printout of the design is cratered and is sent to the implant manufacturer to be built (14) the SRP can support an inventory control of commercially available implant in a way that the hospital purchase the specific implant only after it was tried and verified in the SRP, and only then being ordered from the vendor.

Applications for Image Guided Systems and Operating-Microscopes:

The Surgery Rehearsal Platform (SRP) includes a software module that ties the platform together with Image Guided systems and Operating-Microscopes. By superimposing and projecting the surgery plan that was created by the surgeon using the SRP on the top of the navigation path or the operating-microscopes image, the surgeon is able to follow his own planned actions; such as orientation of the surgery tools, the planned placement and approach of the aneurysm clips and so on.

By push of a button, the surgeon can see in the Image Guided systems or the Operating-Microscopes screen the video clip of the actions that he planes (i) the corridor entry location, corridor approach orientation (ii) the aneurysm clip placement, the aneurysm clip approach of placement, the aneurysm clip orientation (iii) the clip applier and other surgery tools placement, the clip applier and other surgery tools approach of placement, the clip applier and other surgery tools orientation.

This integrated/superimposed image allows surgeons to overcome blocked visibility and hinder visibility challenges that the surgeons may have during the surgery due to the fact that the tools (such as clip applier or other device) may block the surgeons sight and view of the microsurgery site, and thus prevent the surgeon from seeing the vessel or other part on which he operates. The integrated/superimposed image allow the surgeon to repeat the actions that he planned with the SRP in the actual surgery, while overcoming the visual and other challenges allowing a more efficient microsurgery procedure and superior guidance provided to the surgeon, based on his own plan.

Mechanical Integrating of Real Clip Applier

Figure 12:
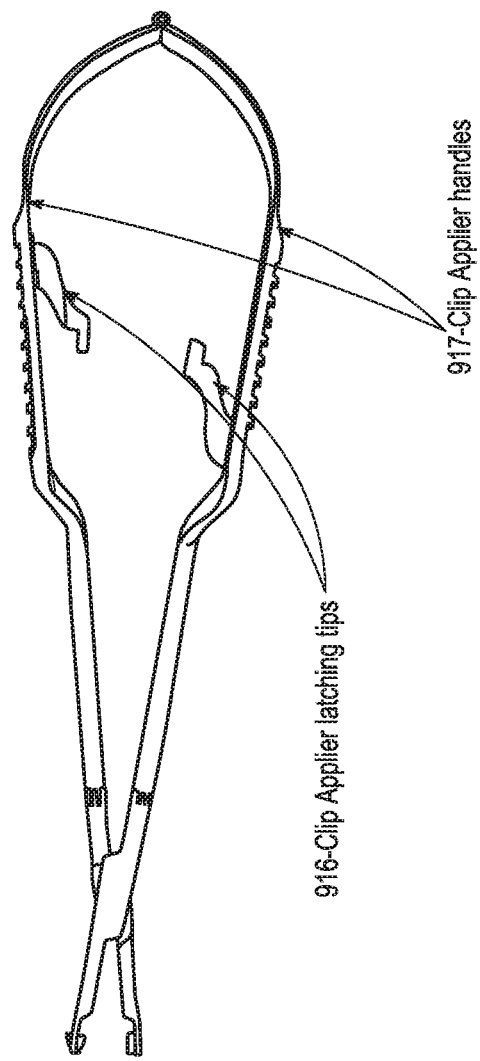
FIG. 12 shows an example real Aneurysm Clip Applier modified to interface with the CA-SRP.
Figure 13:
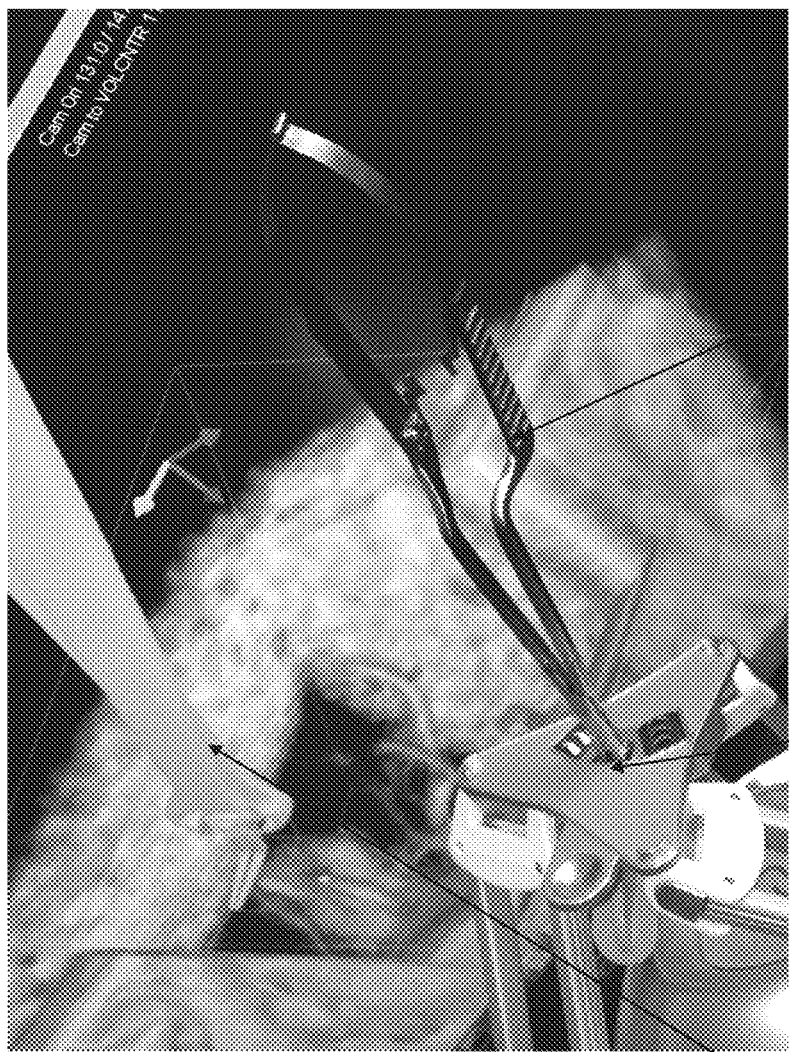
FIG. 13 shows a real Aneurysm Clip Applier that is connected to the system through a tracking, monitoring, and control device/interface along with simulation display for the example CA-SRP.

The system includes an interface to a real surgery tool, as shown in FIG. 13, the Real Clip Applier 919, that is connected to the system through a tracking, monitoring, and Control device/interface 920. This device interface 920 monitors the real clip applier movements and 6 degrees of freedom orientation of the applier (x, y, z and oiler angles pitch, roll, yaw). This interface 920 monitors the applier positing (i.e. close, open or any position in between) action. This interface 920 is connected to the Clip Applier latching tips 916 via the—Clip Applier handles 917, as shown in FIG. 12. Referring again to FIG. 13, the Simulated clip applier 918 is synchronized such that it follows and replies to action taken by the Real Clip Applier 919 transmitted to the simulator by the Tracking, Monitoring and Control device/interface 920.

In the process of the simulated surgery, the surgeon holds the Real Clip Applier 919 and performs the surgery actions, the Simulated clip applier 918 follows, presents, and reflects the surgeon's actions in the simulated environment by synchronized actions of the Simulated clip applier 918 that follows the Real Clip Applier 919. The Real Clip Applier 919 is an example of the way that the system connects a real surgery tool to the simulated environment; other surgery tools such as: CA-SRP's interfaces to the surgeon includes surgery interfaces, o-scissors, by-polars, and bayonet forceps among others. Those interfaces may or may not include force/haptic feedback that is delivered to those tools to allow the surgeon to sense the force feedback cue of his actions.

Clinical Challenges:

Identification and approach to the feeding vessels: Judgment for the optimal placement and orientation of the aneurysm clip to exclude the aneurysms from the cerebral circulation while minimizing the stress on the surrounding vessels.

Choosing specific clips from various clips available: All under sever time constraints. Surgical Theater is allowing surgeons to obtain critical insights for refining the surgery strategy and enhancing the surgery outcomes.

Clinical benefits: The CA-SRP a patient-specific, tailored to each specific case of each patient, preparation tool for surgery, used by surgeons placed in the Neurological surgery department. It is anticipated that the CA-SRP will enhance the surgery outcomes by minimizing surgeries' critical time segments such as the phase of the Aneurysm temporary vessel clamping. The CA-SRP provides an enhanced means to pre-plan the precise clamping orientation and the best course of the approach to the Aneurysm area based on accurate rehearsal as well as selecting the best clip in advance and based on the patient's own anatomy. It is believed that this will result in the quality (efficacy) of the Aneurysm repair to be maximized while adverse events such as strokes are minimized.

Specific clinical benefits: (i) Prior selection of aneurysm clips before even entering the Operating Room (ii) Prior plan of optimal approach to the feeding vessels (iii) Surgeon can perform "what if" scenarios, evaluating different surgery strategies; different clip and different approach. (iv) The surgeon plans the optimal placement and orientation of the aneurysm clip to maximize the exclusion of the aneurysms from the cerebral circulation while minimizing the stress on the surrounding vessels resulting in—improved clinical outcome Enhanced surgery efficiency and Better Outcome and Reduced possibility for adverse events. Furthermore, the CA-SRP is a more than adequate platform for residents and fellows in training and will address several "training related" challenges that our market study tracked. The major training challenge that the CA-SRP will address is the challenge of training brain surgeons with less available hands-on and Operation Room time available due to the restricted duty hours;

Resident's Challenges:

"Residents must not be scheduled for more than 80 duty hours per week"*

*Source: ACGME, 2002 "Many programs have struggled to ensure residents are receiving adequate training since July 2003"++Source: The Nation Congress of Neurological Surgeons Washington Committee The CA-SRP assists residents and fellows to gain more experience by being well prepared in an efficient manner to each patient-specific surgery by utilizing the CA-SRP. The CA-SRP delivers the following benefits, both to the surgeons as well as to the residents and fellows: (1) Reduced surgical adverse events by rehearsing on patient specific simulation with realistic immersive system; and (2) Increasing operational efficiency by reducing surgical duration.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:

1. A modeling system for performing a surgical simulation, comprising:
   a database for storing patient tissue image information that are taken from, or derived from, medical images of a particular patient;
   said database also for storing standard characteristics of said tissue;
   a display;
   an image generator including software executing on one or more computers to generate a dynamic 3D image of tissues of the particular patient for display on said display, said generating utilizing said patient image information such that said dynamic 3D image of tissues realistically represents corresponding actual tissues of the particular patient;
   a tool interface configured to connect to a real surgical tool adapted for use with the modeling system;
   a user tool generator including software executing on the one or more computers to generate a tool model of a user tool for dynamically interacting with said 3D image of tissues via manipulations provided by a user; and
   a user interface configured to allow the user to adjust parameters of the tool model, wherein
   said tool model is displayed on said display dynamically interacting with said 3D image of tissues according to the adjusted parameters for realistically simulating the medical procedure.

2. The modeling system of claim 1, wherein the user interface to adjust parameters allows modifying a structure of said user tool.

3. The modeling system of claim 2, wherein said modifying a structure of said user tool includes changing a shape of said user tool.

4. The modeling system of claim 2, further comprising an interface for outputting specifications for said user tool as modified that are generated by the system.

5. The modeling system of claim 4, wherein said specifications are provided in a format for allowing a manufacture of tools to manufacture an actual user tool designed for use in performing an actual surgery on the patient.

6. The modeling system of claim 1, wherein said medical images of the particular patient include an image of an aneurysm, and wherein said dynamic 3D image includes an image of the aneurysm, and further wherein said user tool includes an aneurysm clip applier for applying an aneurysm clip model for dynamically interacting with the image of tissues.

7. The modeling system of claim 1, further comprising:
   a memory for storing a library of a plurality of models of different implants to the user; and
   a user interface for selecting one implant model from said plurality of models for use with said user tool model for dynamically interacting with said 3D image of tissues.

8. The modeling system of claim 1, wherein said dynamically interacting is provided by executing algorithms adapted for providing segmentation and soft tissue simulation and collision detection for calculating orientation interaction and detecting interaction between the user tool and the 3D image of tissues.

9. The modeling system of claim 1, wherein said system is adapted for displaying an image of at least a portion of the head of the patient on said display, said image of at least a portion of the head being derived from said medical images of the particular patient.

10. The modeling system of claim 1, wherein the user interface to adjust modeling parameters also allows the user to adjust the mechanical properties of the 3D image of tissues.

11. A modeling system for performing a simulation of an aneurysm clipping surgery, comprising:
    a database for storing patient tissue image information that are taken from, or derived from, medical images of a particular patient, said image information including an aneurysm;

said database also for storing standard characteristics of said tissue;

a display;

an image generator including software executing on one or more computers to generate a dynamic 3D image of tissues of the particular patient for display on said display, said generating utilizing said patient image information such that said dynamic 3D image of tissues realistically represents corresponding actual tissues of the particular patient and includes at least one blood vessel showing an image of the aneurysm in 3D;

a tool interface configured to connect to a real aneurysm clip applier adapted for use with the modeling system;

a user tool generator including software executing on one or more computers to generate a tool model of an aneurysm clip applier for dynamically interacting with said image of the aneurysm via manipulations of the real aneurysm clip applier by a user; and a user interface configured to allow the user to adjust modeling parameters of the aneurysm clip model, wherein said aneurysm clip model is displayed on said display dynamically interacting with said 3D image of the aneurysm according to the adjusted modeling parameters for realistically simulating the aneurysm clipping surgery.

12. The modeling system of claim 11, wherein the user interface to adjust modeling parameters of the aneurysm clip model is for modifying a dimension or orientation of said aneurysm clip model.

13. The modeling system of claim 12, wherein said modifying a structure of said aneurysm clip model includes changing a shape of said aneurysm clip model.

14. The modeling system of claim 11, further comprising an interface for outputting specifications for an actual aneurysm clip based on said aneurysm clip model as modified, said specifications being generated by the system.

15. The modeling system of claim 14, wherein said specifications are provided in a format for allowing a manufacture of aneurysm clips to manufacture the actual aneurysm clip for use in performing an actual aneurysm clipping surgery on the patient.

16. The modeling system of claim 11, further comprising:
a memory for storing a library of a plurality of models of different aneurysm clips to the user; and
a user interface for selecting one aneurysm clip model from said plurality of models for use as said aneurysm clip model for dynamically interacting with said image of the aneurysm.

17. The modeling system of claim 11, wherein said dynamically interacting is provided by executing algorithms adapted for providing segmentation and soft tissue simulation and collision detection for calculating orientation interaction and detecting interaction between the model of the aneurysm clip and the aneurysm image.

18. The modeling system of claim 11, wherein said system is adapted for displaying an image of at least a portion of the head of the patient, said image of at least a portion of the head being derived from said medical images of the particular patient.

19. The modeling system of claim 11, wherein the user interface to adjust modeling parameters is also for the user to adjust the mechanical properties of the image of the aneurysm.

20. A modeling system for performing a simulation of an aneurysm clipping surgery, comprising:
a database for storing patient tissue image information that are taken from, or derived from, medical images of a particular patient, said image information including an aneurysm;
said database also for storing standard characteristics of said tissue;
a display;
an image generator including software executing on one or more computers to generate a dynamic 3D image of tissues of the particular patient for display on said display, said generating utilizing said patient image information such that said dynamic 3D image of tissues realistically represents corresponding actual tissues of the particular patient and includes at least one blood vessel showing an image of the aneurysm in 3D;
a memory for storing a library of a plurality of models of different aneurysm clips to a user;
a user interface configured to have the user select one aneurysm clip model from said plurality of models for use as said aneurysm clip model for dynamically interacting with said image of the aneurysm;
a tool interface configured to connect to a real aneurysm clip applier adapted for use with the modeling system;
an interface configured to allow the user to adjust the mechanical properties of the image of the aneurysm;
a user tool generator including software executing on one or more computers to generate a model of an aneurysm clip applier;
said user tool generator also including software executing on one or more computers to generate the selected aneurysm clip model shown dynamically interacting with said model of the aneurysm clip applier applying the model of the aneurysm clip to the image of the aneurysm via manipulations of the real aneurysm clip applier by the user; and
an interface configured to allow the user to adjust mechanical properties of the model of the aneurysm clip and/or the image of the aneurysm, wherein
said aneurysm clip model is displayed on said display dynamically interacting with said 3D image of the aneurysm based on the mechanical properties as adjusted by the user for realistically simulating the aneurysm clipping surgery.

21. A modeling system for performing a surgical simulation, comprising:
one or more processors;
one or more computer-readable tangible storage devices;
a tool interface configured to connect to a real surgical tool adapted for use with the modeling system;
a user interface configured to allow the user to adjust parameters of the tool model; and
program instructions stored on at least one of the one or more storage devices for execution by at least one of the one or more processors, said program instructions comprising:
first program instructions to generate a dynamic 3D image of tissues of the particular patient for display on said display, said generating utilizing said patient image information such that said dynamic 3D image of tissues realistically represents corresponding actual tissues of the particular patient; and
second program instructions to generate a tool model of a user tool for dynamically interacting with said 3D image of tissues via manipulations provided by a user to the real surgical tool, wherein said tool model is displayed on said display dynamically interacting with said 3D image of tissues according to the adjusted parameters for realistically simulating the medical procedure.

* * * * *